(12) United States Patent
Spitler et al.

(10) Patent No.: US 12,042,393 B2
(45) Date of Patent: Jul. 23, 2024

(54) EXPANDABLE INTER VERTEBRAL IMPLANT

(71) Applicant: FloSpine, LLC, Boca Raton, FL (US)

(72) Inventors: James Q. Spitler, Winter Garden, FL (US); Peter M. Harris, Boca Raton, FL (US)

(73) Assignee: FloSpine, LLC, Boca Raton, FL (US)

( * ) Notice: Subject to any disclaimer, the term of this patent is extended or adjusted under 35 U.S.C. 154(b) by 669 days.

(21) Appl. No.: 17/129,237

(22) Filed: Dec. 21, 2020

(65) Prior Publication Data
US 2021/0186706 A1 Jun. 24, 2021

Related U.S. Application Data

(60) Provisional application No. 62/950,180, filed on Dec. 19, 2019.

(51) Int. Cl.
*A61F 2/44* (2006.01)
*A61F 2/30* (2006.01)

(52) U.S. Cl.
CPC ...... *A61F 2/44* (2013.01); *A61F 2002/30072* (2013.01); *A61F 2002/30125* (2013.01);
(Continued)

(58) Field of Classification Search
CPC ...... A61F 2/447; A61F 2/4455; A61F 2/4611; A61F 2002/30579; A61F 2/44;
(Continued)

(56) References Cited

U.S. PATENT DOCUMENTS

| | | |
|---|---|---|
| 6,126,689 A | 10/2000 | Brett |
| 6,443,989 B1 | 9/2002 | Jackson |

(Continued)

FOREIGN PATENT DOCUMENTS

RU 2322212 4/2008

OTHER PUBLICATIONS

International Search Report and Written Opinion dated Nov. 26, 2020 for corresponding International Application No. PCT/US2020/047457.
(Continued)

*Primary Examiner* — Christopher D. Prone
(74) *Attorney, Agent, or Firm* — David Meibos; Maywood IP Law

(57) ABSTRACT

An expandable intervertebral implant is disclosed for use in between adjacent vertebral bodies in a spine. An expandable intervertebral implant may include an upper plate having a first upper side and a second upper side, a lower plate having a first lower side, a second lower side, and a first lattice that connects the first upper side to the first lower side. The expandable intervertebral implant may further include a second lattice that connects the second upper side of the upper plate to the second lower side of the lower plate and an opening having a longitudinal axis between the upper plate, lower plate, first lattice, and second lattice. The expandable intervertebral implant may further include an expansion mechanism comprising a driver that expands the upper plate and the lower plate away from each other along a cephalad-caudal axis by deforming the first lattice and the second lattice.

16 Claims, 12 Drawing Sheets

(52) U.S. Cl.
CPC ............... *A61F 2002/30322* (2013.01); *A61F 2002/30405* (2013.01); *A61F 2002/30579* (2013.01); *A61F 2002/30785* (2013.01); *A61F 2002/3092* (2013.01); *A61F 2/442* (2013.01); *A61F 2/447* (2013.01); *A61F 2310/00023* (2013.01)

(58) Field of Classification Search
CPC .. A61F 2002/30072; A61F 2002/30322; A61F 2002/30405; A61F 2002/3092
See application file for complete search history.

(56) References Cited

U.S. PATENT DOCUMENTS

| | | | |
|---|---|---|---|
| 6,666,891 | B2 | 12/2003 | Boehm, Jr. et al. |
| 7,674,296 | B2 | 3/2010 | Rhoda et al. |
| 9,060,876 | B1 | 6/2015 | To et al. |
| 9,402,733 | B1 | 8/2016 | To et al. |
| 9,750,552 | B2 | 9/2017 | Stephan et al. |
| 9,775,722 | B2 | 10/2017 | Kim et al. |
| 9,907,671 | B2 | 3/2018 | Fessler |
| 9,993,350 | B2 | 6/2018 | Cain |
| 2002/0143401 | A1 | 10/2002 | Michelson |
| 2007/0219634 | A1 | 9/2007 | Greenhalgh et al. |
| 2008/0015693 | A1 | 1/2008 | Le Couedic |
| 2008/0183204 | A1* | 7/2008 | Greenhalgh ....... A61B 17/8858 606/198 |
| 2009/0281628 | A1 | 11/2009 | Oglaza et al. |
| 2010/0106190 | A1 | 4/2010 | Linares |
| 2013/0184754 | A1 | 7/2013 | Taber et al. |
| 2014/0039629 | A1 | 2/2014 | Cipoletti et al. |
| 2015/0127107 | A1 | 5/2015 | Kim et al. |
| 2015/0351925 | A1 | 12/2015 | Emerick et al. |
| 2015/0374508 | A1 | 12/2015 | Sandul |
| 2017/0079695 | A1 | 3/2017 | Zappacosta et al. |
| 2018/0104069 | A1 | 4/2018 | Kim et al. |
| 2018/0116811 | A1 | 5/2018 | Bernard et al. |
| 2018/0125671 | A1 | 5/2018 | Bernard et al. |
| 2019/0231552 | A1 | 8/2019 | Sandul |
| 2019/0336300 | A1 | 11/2019 | Bernard et al. |

OTHER PUBLICATIONS

Globus Medical Launches Aerial, an Expandable Interspinous Fixation Device—Covering the specialized field of orthopedic product development and manufacturing (odtmag.com), May 31, 2019.
International Search Report and Written Opinion dated Apr. 1, 2021 for corresponding International Application No. PCT/US2020/066396.

* cited by examiner

EXPANDABLE INTER VERTEBRAL IMPLANT

CROSS-REFERENCE TO RELATED APPLICATIONS

The present application claims the benefit of U.S. Provisional Patent Application Ser. No. 62/950,180, entitled EXPANDABLE THREADED INTERVERTEBRAL IMPLANT, which was filed on Dec. 19, 2019, which is incorporated by reference as though set forth herein in its entirety.

TECHNICAL FIELD

The present disclosure relates to surgical devices. More specifically, the present disclosure relates to improved surgical devices for implanting expandable intervertebral implants between adjacent vertebral bodies in a patient.

BACKGROUND

Spinal fixation procedures utilizing expandable intervertebral implants can be used to correct spinal conditions such as degenerative disc disease, spondylolisthesis, spinal deformities, or other spinal conditions through minimally invasive or invasive spinal surgery. For example, intervertebral discs can degenerate or otherwise become damaged over time. In some instances, an expandable intervertebral implant can be positioned within a space previously occupied by a disc between adjacent vertebral bodies. Such expandable intervertebral implants can help maintain a desired spacing between adjacent vertebrae and/or promote fusion between adjacent vertebrae. The use of bone graft and/or other materials within an area that includes an expandable intervertebral implant can also facilitate the fusion of adjacent vertebral bodies. Accordingly, a need exists for improved expandable intervertebral implants.

SUMMARY

The various apparatus, devices, systems, and/or methods of the present disclosure have been developed in response to the present state of the art, and in particular, in response to the problems and needs in the art that have not yet been fully solved by currently available expandable intervertebral implants. The apparatus, devices, systems, and/or methods of the present disclosure may provide interspinous-interlaminar stabilization systems and methods that remedy shortcomings of prior art expandable intervertebral implants.

To achieve the foregoing, and in accordance with the disclosure as embodied and broadly described herein, an expandable intervertebral implant may be provided. One general aspect of the expandable intervertebral implant can include an upper plate that may include a first upper side and a second upper side, a lower plate that may include a first lower side and a second lower side, a first lattice that connects the first upper side of the upper plate to the first lower side of the lower plate, a second lattice that connects the second upper side of the upper plate to the second lower side of the lower plate, and an opening having a longitudinal axis between the upper plate, lower plate, first lattice, and second lattice. The expandable intervertebral implant may also include an expansion mechanism that may include a driver that expands the upper plate and the lower plate away from each other along a cephalad-caudal axis by deforming the first lattice and the second lattice.

In one aspect, the opening may have internal threads about the longitudinal axis. In addition, the expansion mechanism can include a screw member that may include a shank having threads that engage the internal threads within the opening. In addition, the screw member can have a diameter selected such that rotation of the screw member about the longitudinal axis by activation of the driver separates the upper plate from the lower plate by deforming the first lattice and the second lattice.

The driver of the expansion mechanism may include a head of the screw member connected to a proximal end of the shank. The screw member may include a tapered end connected to a distal end of the shank and the screw member may have a cross-sectional diameter greater than a height of the opening. The cross-sectional diameter of the screw member can be greater than a width of the opening.

In one aspect, the expansion mechanism may include a set of screw members and each can have a shank that includes threads that engage the internal threads within the opening. Each screw member of the set of screw members can have a different cross-sectional diameter.

The upper plate may have an upper lattice and the lower plate may have a lower lattice. The expansion mechanism can be configured such that activation of the expansion mechanism by the driver expands the upper plate and the lower plate away from each other along the cephalad-caudal axis. In addition, or alternatively, activation of the expansion mechanism may also move the first lattice and the second lattice away from each other along a medial-lateral axis by deforming the first lattice, the second lattice, the upper lattice, and the lower lattice.

The opening may have an ovoid cross-section that may have a height that is different from a width of the ovoid cross-section.

The first lattice and the second lattice may be made of metal. The first lattice and the second lattice each have a common pattern. The pattern, and/or the common pattern, may have one or more of a set of geometric shapes that include pores.

One general aspect can include an expandable intervertebral implant that may have an upper plate that may have an upper mesh, a first upper side, and a second upper side, a lower plate that may have a lower mesh, a first lower side, and a second lower side, a first wall that connects the first upper side of the upper plate to the first lower side of the lower plate, the first wall may have a first mesh, a second wall that connects the second upper side of the upper plate to the second lower side of the lower plate, the second wall may have a second mesh, an opening having a longitudinal axis between the upper plate, the lower plate, the first wall, and the second wall, and an expansion mechanism that may have a driver that expands the upper plate and the lower plate away from each other along a cephalad-caudal axis by expanding the first mesh and the second mesh and moves the first wall and the second wall away from each other along a medial-lateral axis by expanding the upper mesh and the lower mesh.

Certain embodiments may include one or more of the following aspects. The opening may have internal threads about the longitudinal axis and the expansion mechanism may have a screw member that may include a shank that may have threads that engage the internal threads within the opening, the screw member having a diameter selected such that rotation of the screw member about the longitudinal axis by activation of the driver expands, the first mesh, the second mesh, the upper mesh, and the lower mesh.

The opening may have an elliptical cross-section that may have a height that is smaller than a width of the elliptical cross-section. The first mesh and the second mesh may each have a first pattern. The first pattern and the height of the elliptical cross-section of the opening may each be selected such that activation of the driver of the expansion mechanism causes a predetermined increase in distance, a predetermined spacing, between the upper plate and the lower plate.

In one aspect, the first mesh and the second mesh may each have a first pattern and the upper mesh and the lower mesh may each have a second pattern. The first pattern and the second pattern may each be selected such that activation of the driver of the expansion mechanism causes a first predetermined increase in a distance between the upper plate and the lower plate that differs from a second predetermined increase in a distance between the first wall and the second wall.

The expandable intervertebral implant may have a proximal end and a distal end. The first mesh may span the first wall from the first upper side to the first lower side and from the proximal end to the distal end of the expandable intervertebral implant. The second mesh may span the second wall from the second upper side to the second lower side and from the proximal end to the distal end of the expandable intervertebral implant. The upper mesh may span the upper plate from the first upper side to the second upper side and from the proximal end to the distal end of the expandable intervertebral implant. The lower mesh may span the lower plate from the first lower side to the second lower side and from the proximal end to the distal end of the expandable intervertebral implant.

One general aspect can include an expandable intervertebral implant that may have an upper plate that may have an upper lattice, a first upper side, and a second upper side, a lower plate that may have a lower lattice, a first lower side and a second lower side, a first lattice that connects the first upper side of the upper plate to the first lower side of the lower plate, a second lattice that connects the second upper side of the upper plate to the second lower side of the lower plate, an opening having internal threads about a longitudinal axis between the upper plate, the lower plate, the first lattice, and the second lattice, and a screw member that may have a shank that may have threads that engage the internal threads within the opening, the screw member having a diameter such that rotation of the screw member about the longitudinal axis separates the upper plate from the lower plate by deforming the first lattice and the second lattice and separates the first lattice from the second lattice by deforming the upper lattice and the lower lattice.

The upper plate, the lower plate, the first lattice, and the second lattice may be made from titanium. The first lattice and the second lattice may each include a first pattern, a size of the opening, and a diameter of the screw member selected such that that rotation of the screw member about the longitudinal axis moves the screw member within the opening and expands the expandable intervertebral implant along a cephalad-caudal axis and along a medial-lateral axis to a target expanded configuration.

Certain embodiments, of the expandable intervertebral implant may further include a proximal end, a distal end, and an inserter attachment feature connected to the upper plate, the lower plate, the first lattice, and the second lattice at the proximal end. The upper lattice, the lower lattice, the first lattice, and the second lattice each extend to include the inserter attachment feature. In other words, a pattern for one or more of the upper lattice, the lower lattice, the first lattice, and the second lattice may also be formed within one or more walls of the inserter attachment feature.

These and other features and advantages of the present disclosure will become more fully apparent from the following description and appended claims or may be learned by the practice of the disclosure as set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

Figure 1A:
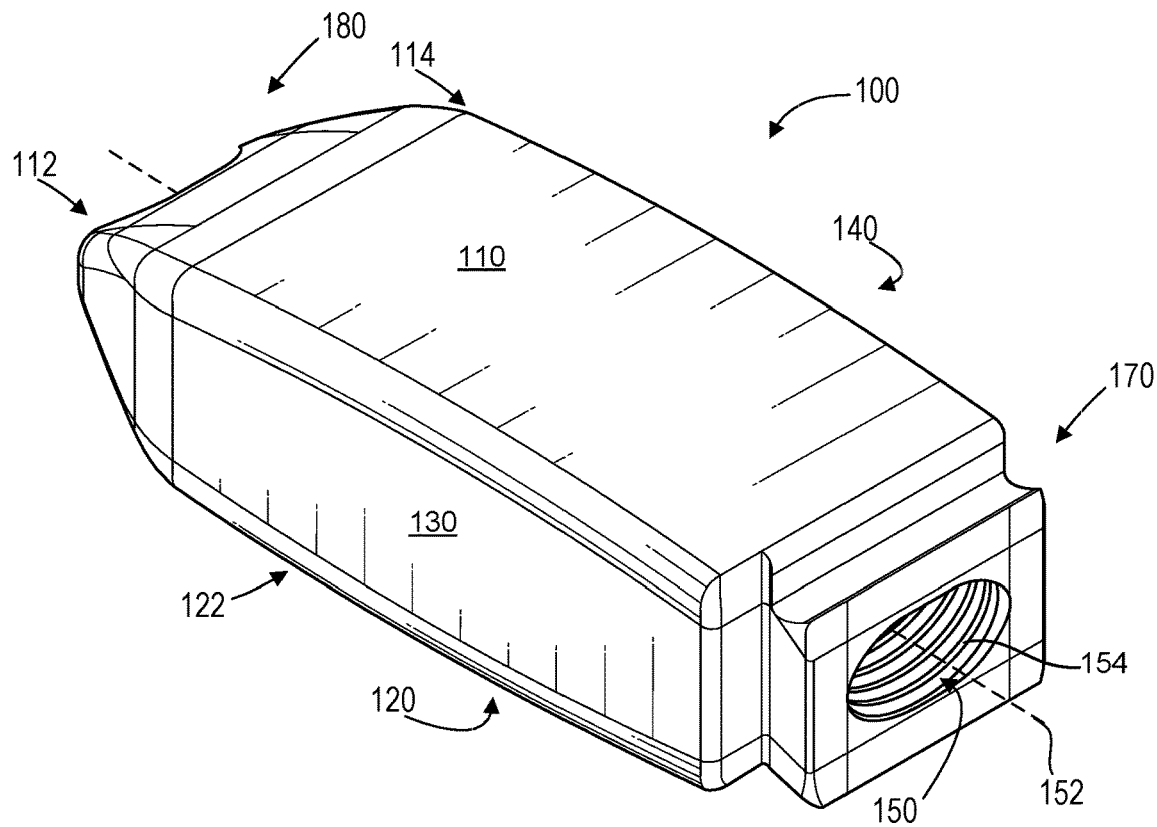
FIG. 1A is a perspective top view of a proximal end of an expandable intervertebral implant 100, according to one embodiment of the present disclosure.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The present disclosure discloses an expandable intervertebral implant. Medical procedures for using expandable intervertebral implants favor an expandable intervertebral implant that is small and compact. For example, minimally invasive or invasive surgery on the spine, such as spinal fusion, may be use a variety of approaches to access the spine, examples include Anterior Lumbar Interbody Fusion (ALIF), Posterior Lumbar Interbody Fusion (PLIF), or Lateral Interbody Fusion (LIF). For each of these spinal procedures, a smaller implant that can be expanded, as needed, to a desired height and/or width, is preferred because the smaller expandable intervertebral implants can cause less disruption of soft tissue and smaller access openings can be used for the procedures.

For example, using a smaller expandable intervertebral implant for minimally invasive spine (MIS) surgery techniques can reduce the size of the incisions, soft tissue damage, blood loss, less intrusive implants, post-operative pain, recovery time, risk of surgical complications, and the like. Furthermore, the shape, or profile, of an expandable intervertebral implant can facilitate insertion of the implant during the surgery and provide more stable and secure engagement between the implant and vertebral bodies on either side of a space where the implant is positioned.

For example, using a smaller expandable intervertebral implant having fewer parts can result in a more reliable and effective expandable intervertebral implant. Expandable intervertebral implant with fewer parts can be less expensive to fabricate and can be less prone to failure. These and other unique features of the expandable intervertebral implant are discussed below and illustrated in the accompanying drawings.

For example, in one embodiment, the expandable intervertebral implant may have two parts, a structure for the expandable intervertebral implant and an expansion mechanism, such as a screw member. An expandable intervertebral implant that includes just a structure that forms the expandable intervertebral implant, and the expansion mechanism can be simpler than other implants and can be easier to operate and install during a surgical procedure. In addition, certain embodiments of the expandable intervertebral implant may include an expansion mechanism that includes a plurality of screw members, each having a different diameter. In such an embodiment, a surgeon can choose which diameter screw member to use to achieve a target expanded configuration. Of course, one skilled in the art may recognize other situations and advantages of an expandable intervertebral implant having a minimal number of parts; this disclosure contemplates all such situations and advantages.

Similarly, an expandable intervertebral implant having fewer parts may be fabricated with smaller dimensions in a collapsed configuration. A smaller expandable intervertebral implant can enable MIS surgery techniques that use a narrower incision and/or narrower cannulas to perform the procedure. A smaller expandable intervertebral implant can facilitate positioning and placement of the implant. In certain circumstances two or more expandable intervertebral implants may be used to provide desired support for vertebral bodies.

FIG. 1A is a perspective view depicting one exemplary embodiment of an expandable intervertebral implant 100. The expandable intervertebral implant 100 may generally include an upper plate 110 configured to engage a superior vertebral body (not shown), a lower plate 120 configured to engage an inferior vertebral body (not shown), a first lattice 130, a second lattice 140, an opening 150, and an expansion mechanism 160. The expandable intervertebral implant 100 can further include a proximal end 170 and a distal end 180.

As used herein, a "plate" refers to a flat structure. In certain embodiments, a plate can be configured to support a load. In certain embodiments, a plate may comprise a generally planar structure. A plate can be a separate structure connected to, or integrated with, another structure. Alternatively, a plate can be connected to part of another structure. A plate be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. A plate can be made from a variety of materials including, metal, plastic, ceramic, wood, fiberglass, or the like.

One plate may be distinguished from another based on where the plate is positioned within a structure, component, or apparatus. For example, an "upper plate" can include a plate positioned on, near, or integrated with, a structure such that the plate is at, or near, a top of the structure. Similarly, a "lower plate" can include a plate positioned on, near, or integrated with, a structure such that the plate is at, or near, a bottom of the structure.

In the illustrated embodiment, the upper plate 110 can be a superior structure of the expandable intervertebral implant 100. The upper plate 110 can be a three-dimensional rectangular structure having a generally planar external surface. The lower plate 120 can be an inferior structure of the expandable intervertebral implant 100. The lower plate 120 can be a three-dimensional rectangular structure having a generally planar external surface. In the illustrated embodiment, the upper plate 110 and lower plate 120 can have the same or a similar length and width.

The upper plate 110 may include a first upper side 112 and a second upper side 114. As used herein, a "side" refers to a location on a structure. In general, a side is a location on a structure at, or near, a furthest position away from a central axis of the structure. In one embodiment, the first upper side 112 is at, or near, a longitudinal edge of the upper plate 110 and the second upper side 114 is at, or near, an opposite longitudinal edge of the upper plate 110.

Figure 1B:
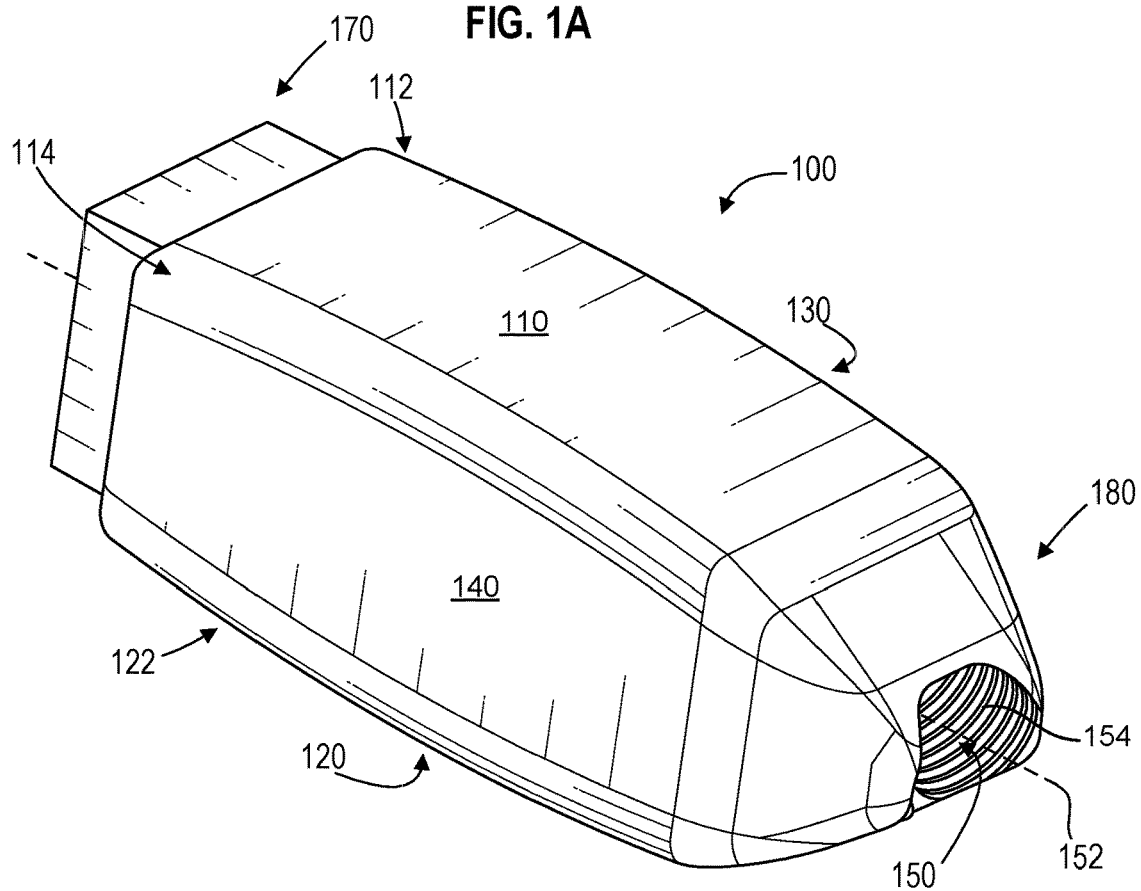
FIG. 1B is a perspective top view of a distal end of the expandable intervertebral implant 100 of FIG. 1A.

The lower plate 120 may include a first lower side 122 and a second lower side 124 (See FIG. 1B). In one embodiment, the first lower side 122 is at, or near, a longitudinal edge of the lower plate 120 and the second lower side 124 is at, or near, an opposite longitudinal edge of the lower plate 120.

The first lattice 130 can form one wall of the expandable intervertebral implant 100. As used herein, a "lattice" refers to a three-dimensional planar structure having a plurality of pores distributed within a longitudinal plane of the structure. Furthermore, the pores of the lattice are configured to expand and/or compress in response to a tensile force or compressive force applied in opposite directions and at opposite ends of the lattice. In particular embodiments, structures of the lattice that interconnect the pores are configured and made of a material that is elastic such that lattice expands its overall shape in response to tensile force(s) and or contracts its overall shape in response to compressive force(s). In certain embodiments, a tensile force on the lattice in opposite directions and at opposite ends causes the lattice to deform, or stretch, to have a greater surface area.

In certain embodiments, the pores of the lattice comprise at least one shape. For example, in one embodiment, each of the pores can have a geometric shape, a polygon shape, a circular shape, an ovoid shape, an elliptical shape, and the like. In certain embodiments, a "lattice" may comprise a "mesh." As used herein, a "mesh" refers to a three-dimensional planar structure having a plurality of openings distributed within a longitudinal plane of the structure. Each of the plurality of openings of the mesh may be of a common shape. Alternatively, or in addition, the plurality of openings of a mesh may include openings having two or more geometric shapes.

FIG. 1A illustrates the first lattice 130 in general without the pores specifically illustrated, at least in part, because the first lattice 130 can have a variety of different kinds, types, sizes, numbers, formats, designs, and distribution arrangements of the pores. Thus, FIG. 1A illustrates a generic lattice for the first lattice 130 and/or FIG. 1B illustrates a generic lattice for the second lattice 140. A few variations and/or embodiments for the first lattice 130 and/or second lattice 140 will be described in more detail herein, however, the claims of this disclosure are not limited to the embodiments illustrated or described.

FIG. 1A illustrates that the first lattice 130 provides structural support and definition to the expandable intervertebral implant 100 and connects the first upper side 112 of the upper plate 110 to the first lower side 122 of the lower plate 120.

FIG. 1B illustrates that the second lattice 140 provides structural support and definition to the expandable intervertebral implant 100 and connects the second upper side 114 of the upper plate 110 to the second lower side 124 of the lower plate 120.

The expandable intervertebral implant 100 can include an opening 150. As used herein, an "opening" refers to a gap, a hole, an aperture, a void in a structure, or the like. In certain embodiments, an opening can refer to a structure configured specifically for receiving something and/or for allowing access. In one embodiment, the opening 150 extends from the proximal end 170 to the distal end 180 of the expandable intervertebral implant 100. The opening 150 can include a longitudinal axis 152 that extends from one end of the opening 150 to the other. The opening 150 is between the upper plate 110, the lower plate 120, the first lattice 130, and the second lattice 140. In certain embodiments, the longitudinal axis 152 can run through a geometric center of a cross-section of the opening 150.

Figure 5A:
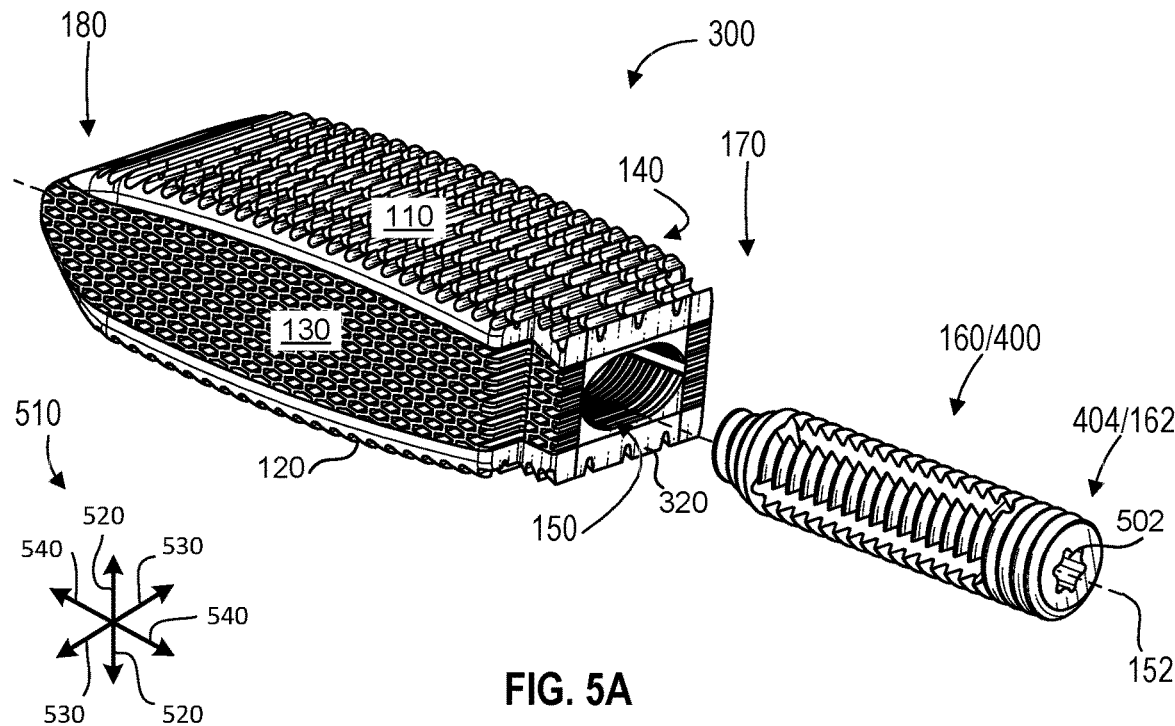
FIG. 5A is an exploded view of the expandable intervertebral implant 300 of FIG. 3A with the screw member of FIG. 4A.

In certain embodiments, the opening 150 is configured and/or sized to receive an expansion mechanism 160 and/or a component of an expansion mechanism 160 (See FIG. 5A). As will be appreciated by those of skill in the art, in this disclosure, the opening 150 can receive a variety of different types of expansion mechanisms 160. In the illustrated embodiment, the opening 150 includes internal threads 154 about the longitudinal axis 152. The internal threads 154 can be configured and arranged to engage with threads of an expansion mechanism 160. One exemplary expansion mechanism 160 is described in more detail in relation to subsequent Figures. Other suitable examples of an expansion mechanism 160 include, but are not limited to a peg, a wedge, a pin, or the like. Those of skill in the art may recognize other suitable expansion mechanisms 160 that can be used in connection with the opening 150.

In certain embodiments, the expansion mechanism 160 can include a driver 162 (See FIG. 5A). A driver 162 is a component of the expansion mechanism 160 configured to expand or contract the expansion mechanism 160 when the driver 162 is activated or de-activated. In one embodiment, the driver 162 is configured to expand the upper plate 110 and the lower plate 120 away from each other along a cephalad-caudal axis (See FIG. 5A) by deforming the first lattice 130 and the second lattice 140. Further description of the driver is provided in relation to FIGS. 4A,5A.

FIG. 1A is a perspective top view from the proximal end 170 of the expandable intervertebral implant 100 and FIG. 1B is a perspective top view from the distal end 180 of the expandable intervertebral implant 100 of FIG. 1A. The distal end 180 of the expandable intervertebral implant 100 is an end that first enters the space between two vertebral bodies as a surgeon installs the expandable intervertebral implant 100. The proximal end 170 of the expandable intervertebral implant 100 is an end of the expandable intervertebral implant 100 closest to a surgeon installing the expandable intervertebral implant 100 between two vertebral bodies. The proximal end 170 is near an end of the expandable intervertebral implant 100 that includes a removably connects to an insertion tool used to install the expandable intervertebral implant 100.

In certain embodiments, the expandable intervertebral implant 100 and its components can be made from the same material. Alternatively, or in addition, the upper plate 110, lower plate 120, first lattice 130, and second lattice 140 can be made from different materials. For example, the first lattice 130 and second lattice 140 can be made from a material having a different plasticity than the upper plate 110 and/or lower plate 120. In one embodiment, the first lattice 130 and second lattice 140 can be made from a material having a common plasticity such that first lattice 130 and second lattice 140 deform together under and expansion force created by the expansion mechanism 160.

The expandable intervertebral implant 100 and/or its constituent components may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. In one embodiment, the first lattice 130 and/or the second lattice 140 can be made of metal. In some embodiments, components of the expandable intervertebral implant 100 may be formed of a less rigid material so that the upper plate 110 and/or lower plate 120 can spread apart from each other in response to the expansion mechanism 160.

The expandable intervertebral implant 100 and/or its constituent components may be manufactured using any known manufacturing method, including casting, forging, milling, additive manufacturing, and/or the like. As used herein, "additive manufacturing" refers to a manufacturing process in which materials are joined together in a process that repeatedly builds one layer on top of another to generate a three-dimensional structure or object. Additive manufacturing may also be referred to using different terms including: additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, biochemicals, and the like. Additive manufacturing may provide unique benefits, as the expandable intervertebral implant 100 together with the pores of the lattices 130/140 can be directly manufactured (without the need to generate molds, tool paths, perform any milling, and/or other manufacturing steps).

Figure 2A:
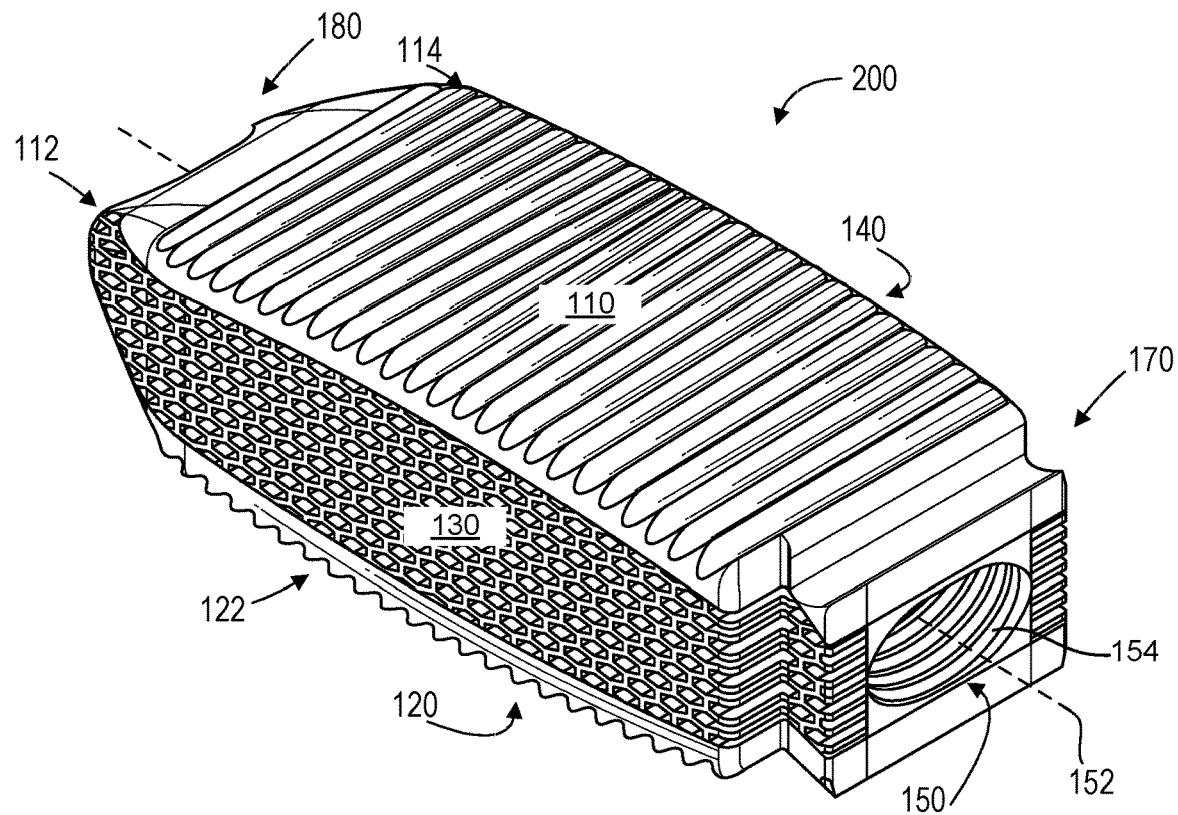
FIG. 2A is a perspective top view of a proximal end of an expandable intervertebral implant 200, according to one embodiment of the present disclosure.

FIG. 2A is a perspective top view of a proximal end of an expandable intervertebral implant 200, according to one embodiment of the present disclosure. In the illustrated embodiment, like parts are identified by common numbers in other figures. The embodiment of FIG. 2A includes an upper plate 110, a lower plate 120, a first lattice 130, a second lattice 140, an opening 150, and an expansion mechanism 160 as described in relation to FIGS. 1A and 1B.

Figure 2B:
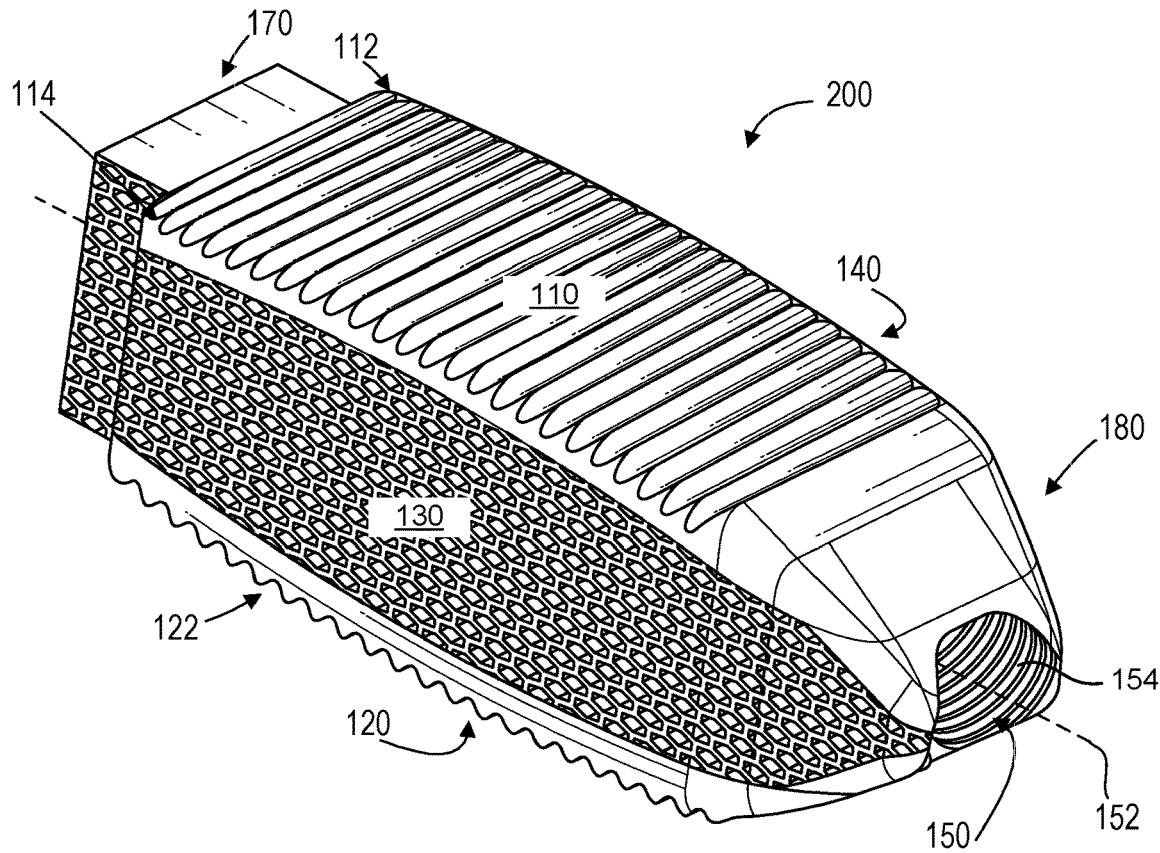
FIG. 2B is a perspective top view of a distal end of the expandable intervertebral implant 200 of FIG. 2A.

In addition, FIGS. 2A and 2B illustrate details of the first lattice 130 and the second lattice 140. Specifically, the first lattice 130 and the second lattice 140 each have a pattern. As used herein, "pattern" refers to a repeated set of shape, shapes, or design within or upon a planar structure. In certain embodiments, the pattern defines the number, size, position, layout, and distribution of shapes of the lattice. The shapes of the pattern for the lattice can include the openings and/or pores of the lattice. In one embodiment, the pattern includes a distributed set of pores, or shapes, or openings, that include one or more geometric shapes of a set of geometric shapes. In certain embodiments, the set of pores of the opening is uniformly distributed. In other embodiments, the set of pores of the opening is non-uniformly distributed.

In one embodiment, the pattern for the first lattice 130 can be different from the pattern for the second lattice 140. In another embodiment, the first lattice 130 and second lattice 140 both have a common pattern. In the illustrated exemplary embodiment, the first lattice 130 and the second lattice 140 each include a pattern of pores/openings shaped as hexagons.

In an embodiment, where the first lattice 130 and second lattice 140 both have the same pattern or a common pattern, activation of the expansion mechanism 160 can cause both the first lattice 130 and the second lattice 140 to expand in an even, uniform, and predictable manner. Consequently, the upper plate 110 and lower plate 120 can maintain a parallel relationship to each other when the expansion mechanism 160 changes the expandable intervertebral implant 100 from a collapsed configuration to an expanded configuration.

Figure 3A:
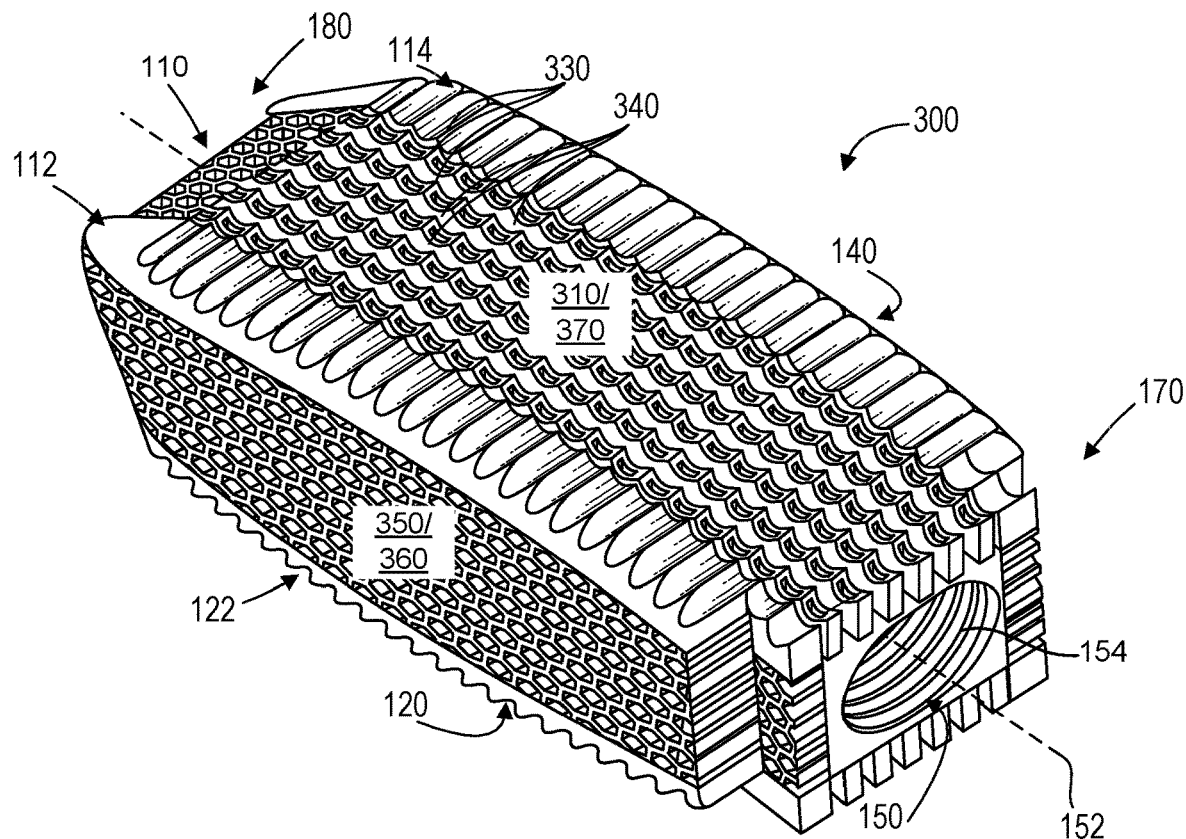
FIG. 3A is a perspective top view of a proximal end of an expandable intervertebral implant 300, according to one embodiment of the present disclosure.
Figure 3B:
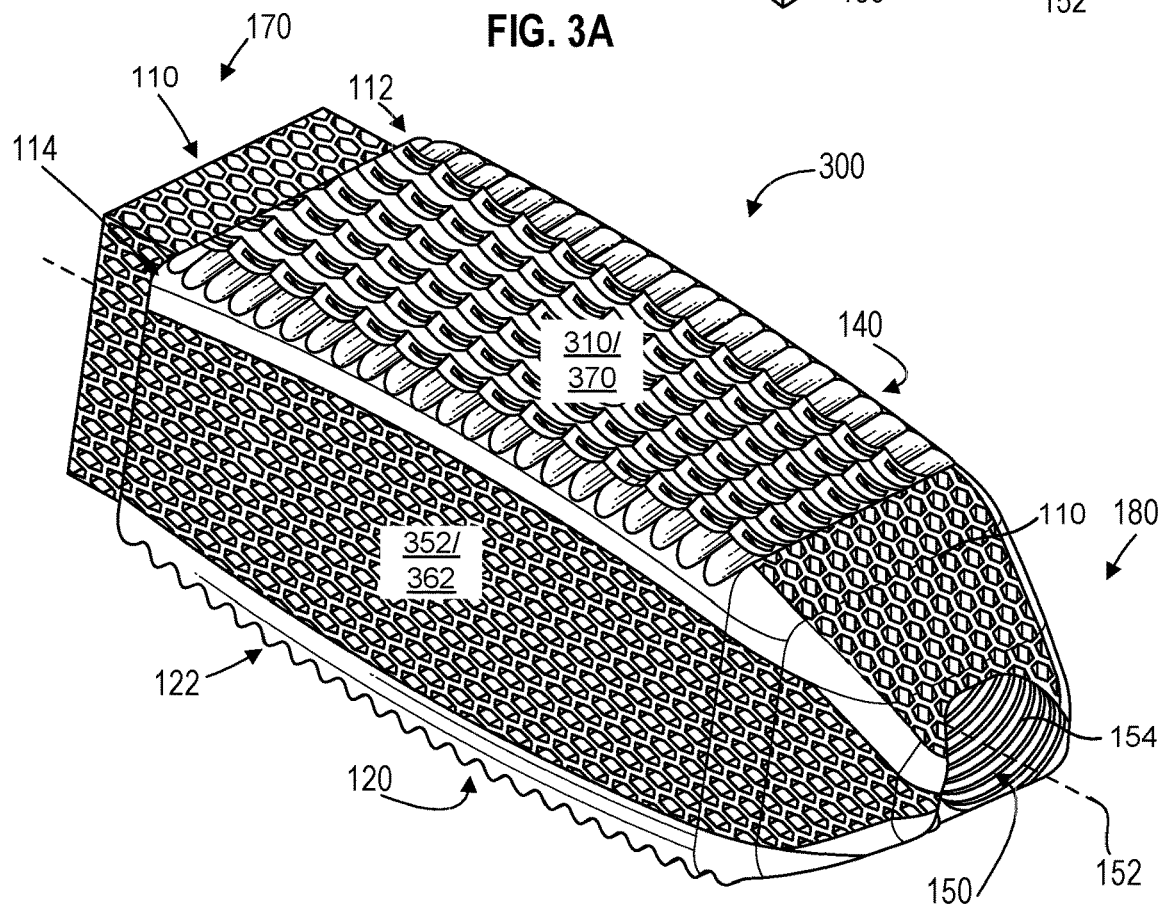
FIG. 3B is a perspective top view of a distal end of the expandable intervertebral implant 300 of FIG. 3A.

FIG. 3A is a perspective top view of a proximal end 170 of an expandable intervertebral implant 300, according to one embodiment of the present disclosure. FIG. 3B is a perspective top view of a distal end 180 of the expandable intervertebral implant 300 of FIG. 3A. In the illustrated embodiment, like parts are identified by common numbers in other figures. The embodiment of FIG. 3A includes an upper plate 110, a lower plate 120, a first lattice 130, a second lattice 140, an opening 150, and an expansion mechanism 160 as described in relation to FIGS. 1A and 1B.

In addition, as illustrated in the expandable intervertebral implant 300 of FIG. 3A, the upper plate 110 includes an upper lattice 310 and the lower plate 120 includes a lower lattice 320. In certain embodiments, the upper lattice 310 and lower lattice 320 can have the same pattern as the first lattice 130 and/or second lattice 140. Alternatively, the upper lattice 310 and lower lattice 320 can each have a common pattern different from one of the patterns of the first lattice 130 and/or second lattice 140.

As will be discussed in more detail later, the upper lattice 310 and lower lattice 320 enable expansion of the first lattice 130 and the second lattice 140 away from each other along a medial-lateral axis (shown in FIG. 5A). In this manner, the expandable intervertebral implant 300 is configured to expand in four directions when the expansion mechanism 160 is activated.

In certain embodiments, the upper plate 110 includes a plurality of teeth 330 and a plurality of grooves 340. The plurality of teeth 330 can connect to the upper plate 110 along a surface of the upper plate 110. The plurality of grooves 340 can run perpendicular to the plurality of teeth 330. The plurality of teeth 330 and plurality of grooves 340 can serve to engage a superior vertebral body.

Figure 3C:
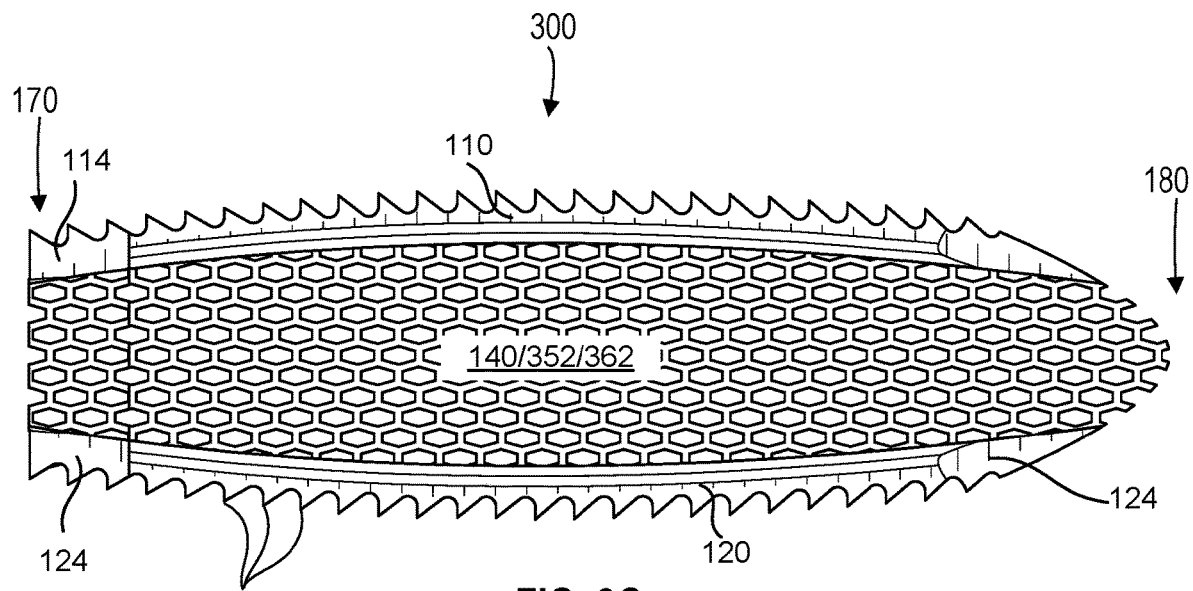
FIG. 3C is a side elevation view of the expandable intervertebral implant 300 of FIG. 3A.

Similarly, the lower plate 120 can include a plurality of teeth 330 and a plurality of grooves (See FIG. 3C). The plurality of teeth 330 can connect to the lower plate 120 along a surface of the lower plate 120. The plurality of teeth 330 serve to engage an inferior vertebral body. The number of teeth 330 and/or their positions on the upper plate 110 and/or lower plate 112 may vary in certain embodiments of an expandable intervertebral implant 100, 200, 300. In the illustrated embodiment of FIGS. 1A-3D, the teeth 330 each point towards the proximal end 170. Of course, those of skill in the art recognize that other positions, patterns, placement and spacing of the plurality of teeth 330 and/or the plurality of grooves 340 may be used with the expandable intervertebral implant disclosed herein.

Figure 3D:
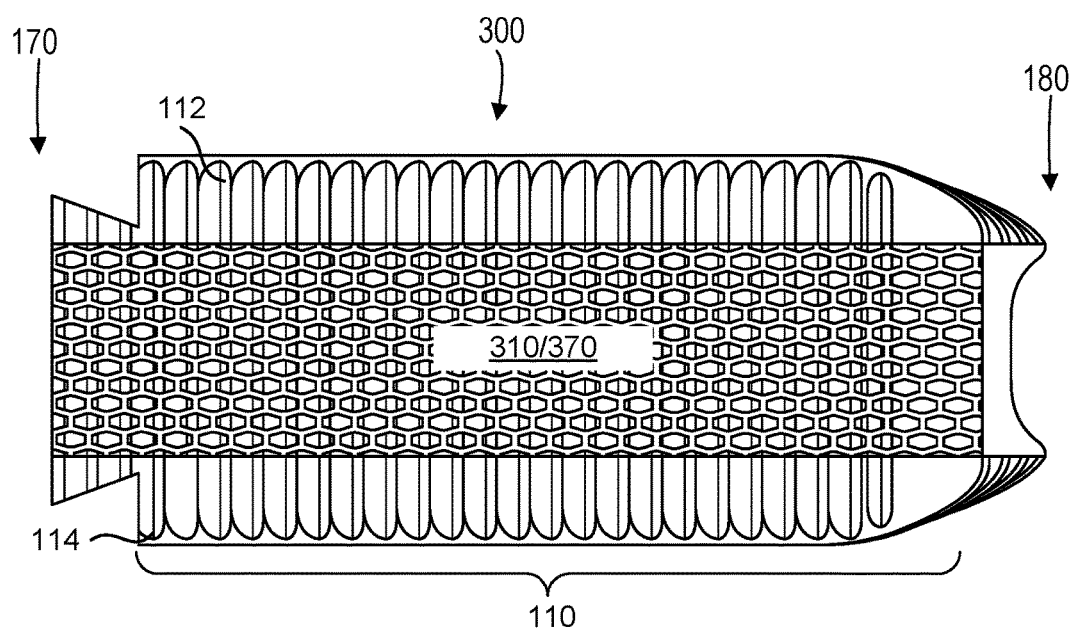
FIG. 3D is a plan view of the expandable intervertebral implant 300 of FIG. 3A.

FIG. 3C is a side elevation view of the expandable intervertebral implant 300 of FIG. 3A and FIG. 3D is a plan view of the expandable intervertebral implant 300 of FIG. 3A. In certain embodiments, the expandable intervertebral implant 300 is symmetrical between its upper plate 110 and lower plate 120 and between its first lattice 130 and second lattice 140. Therefore, as FIG. 3C illustrates a second lattice 140 and FIG. 3D illustrates a upper plate 110, those of skill in the art will recognize and understand the configuration of the symmetrical first lattice 130 and lower plate 120.

Referring to FIGS. 3A-3D, in certain embodiments, a first wall 350 can be used in place of a first lattice 130 and a second wall 352 used in place of a second lattice 140. The first wall 350 can include a first mesh 360 and the second wall 352 can include a second mesh 362. In addition, an upper mesh 370 can be used in place of an upper lattice 310 and a lower mesh 380 in place of a lower lattice 320. FIG. 3A illustrates the second lattice 140 or second wall 352. Similarly, FIG. 3B illustrates an upper lattice 310 or upper mesh 370.

FIG. 3C illustrates that the lattice or mesh of wall may extend from a proximal end 170 to a distal end 180 of the expandable intervertebral implant 300. Similarly, FIG. 3D illustrates that the upper mesh and/or lower mesh of an upper plate 110 and/or lower plate 120 may extend from the proximal end 170 to the distal end 180.

Figure 4A:
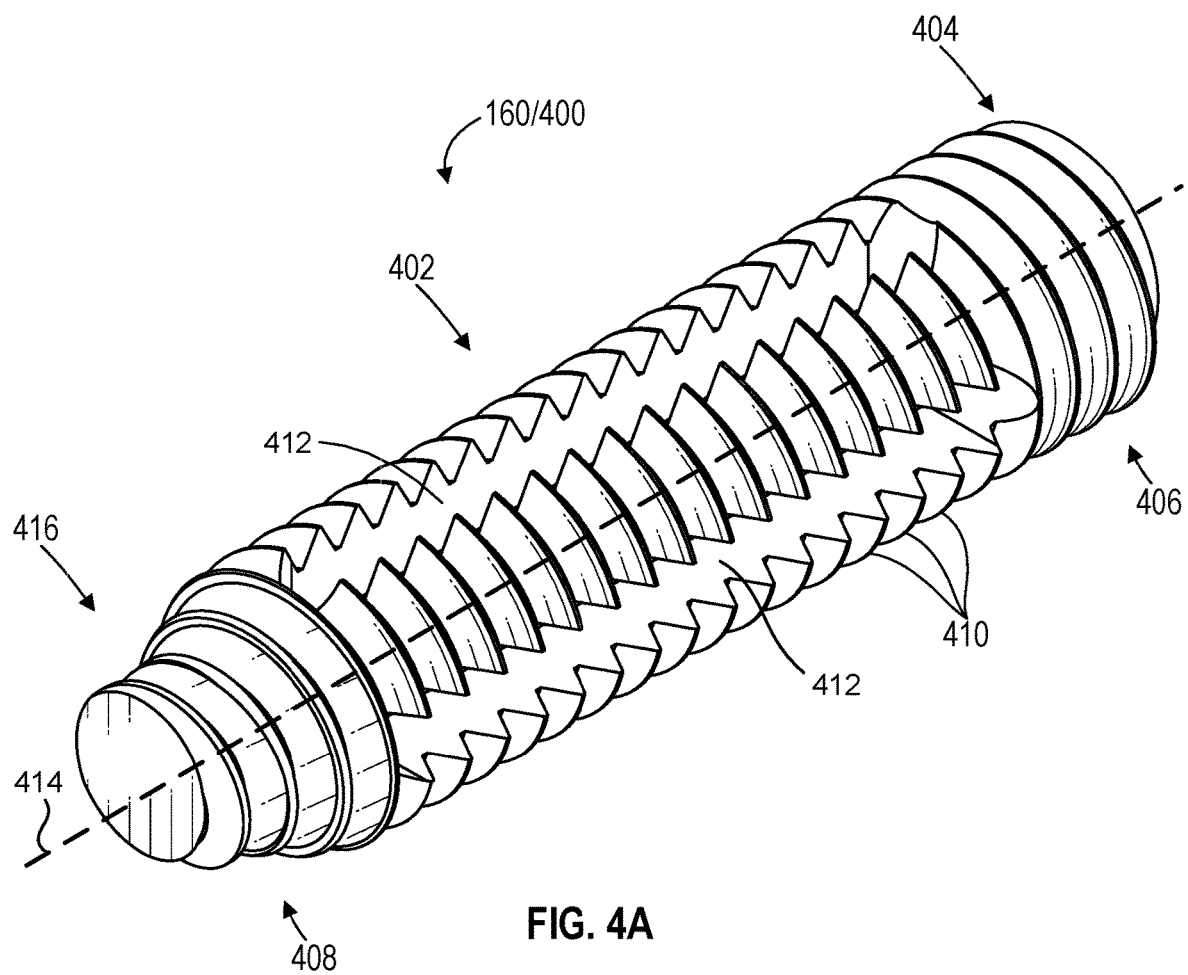
FIG. 4A is a perspective view of a distal end of an expansion mechanism according to one embodiment of the present disclosure.

FIG. 4A is a perspective view of a distal end of an expansion mechanism 160 according to one embodiment of the present disclosure. The expansion mechanism 160 may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. In some embodiments, the expansion mechanism 160 may be formed of different materials than the expandable intervertebral implant 100. For example, the expansion mechanism 160 may be formed a material that is suitably strong enough to withstand torque applied to the driver 162 of the expansion mechanism 160 to activate the driver 162.

In one embodiment, the expansion mechanism 160 includes a screw member 400. The screw member 400 includes a shank 402, a head 404, a proximal end 406, and a distal end 408.

The shank 402 is a narrow structure that joins the head 404 with the distal end 408. In one embodiment, the shank 402 includes threads 410. The threads 410 are configured to engage with internal threads 154 of the opening 150. The threads 410 may extend from the proximal end 406 to the distal end 408. Alternatively, the threads 410 may extend from the distal end 408 part way along the shank 402. In the illustrated embodiment, the shank 402 includes one or more slots 412. The slots 412 may extend along a length of the shank 402 and may pass through the shank 402 from one side to the opposite side. The slots 412 may facilitate bone growth through the expandable intervertebral implant as part of a recovery process once the expandable intervertebral implant is installed in a patient.

In one embodiment, the head 404 serves as the driver 162 of the expansion mechanism 160. The head 404 can be at the proximal end 406 of the screw member 400. The head 404 can be used to rotate the screw member 400 about a longitudinal axis 414 of the screw member 400 to activate the expansion mechanism 160.

The screw member 400, in certain embodiments, may include a tapered end 416 at the distal end 408. The tapered end 416 facilitates placement and alignment of the screw member 400 with an opening 150 of an expandable intervertebral implant of this disclosure.

Figure 4B:
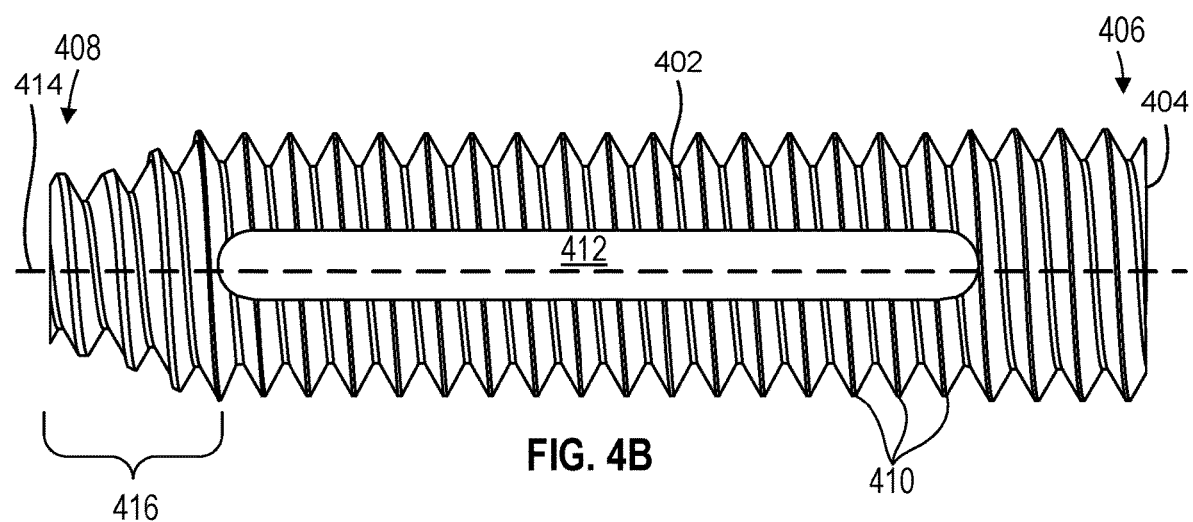
FIG. 4B illustrates a side elevation view of the expansion mechanism of FIG. 4A.

FIG. 4B illustrates a side elevation view of the screw member 400 of FIG. 4A. FIG. 4B illustrates that the head 404 connects to a proximal end 406 and the tapered end 416 connects to a distal end 408. In certain embodiments, the screw member 400 has a circular cross section. As described in more details below, a cross-section of the screw member 400 has a greater diameter than one or more of a height and a width of the opening 150. The greater height causes the expandable intervertebral implant to expand as the screw member 400 enters the opening 150.

FIG. 5A is an exploded view of the expandable intervertebral implant 300 of FIG. 3A with the screw member 400 of FIG. 4A. The expandable intervertebral implant 300 is in a collapsed configuration. FIG. 5A illustrates an expansion mechanism 160 embodied as a screw member 400 configured to engage internal threads 154 and seat within the opening 150 at the proximal end 170. In certain embodiments, the internal threads 154 may be considered a part of the expansion mechanism 160. Alternatively, or in addition, certain embodiments of the expansion mechanism 160 may not require internal threads 154.

FIG. 5A illustrates an embodiment of the screw member 400 with a head 404 that includes a drive recess 502 on one end of the head 404. The drive recess 502 is configured to receive a drive member of an inserter tool (not shown) used to install the expandable intervertebral implant. The drive recess 502 can be configured to have any one of a variety of shapes including slotted, Torx, Torx plus, Philips, Quadrex, Pozidriv, square recess, tri-wing, spanner, or the like. The drive recess 502 can be centered on a longitudinal axis of the screw member 400 which aligns with the longitudinal axis 152 when the screw member 400 is inserted into the opening 150. Of course, those of skill in the art recognize that the shape and configuration of the drive member and the drive recess 502 can be reversed and thus comprise an embodiment within the scope of the present disclosure.

Figure 5B:
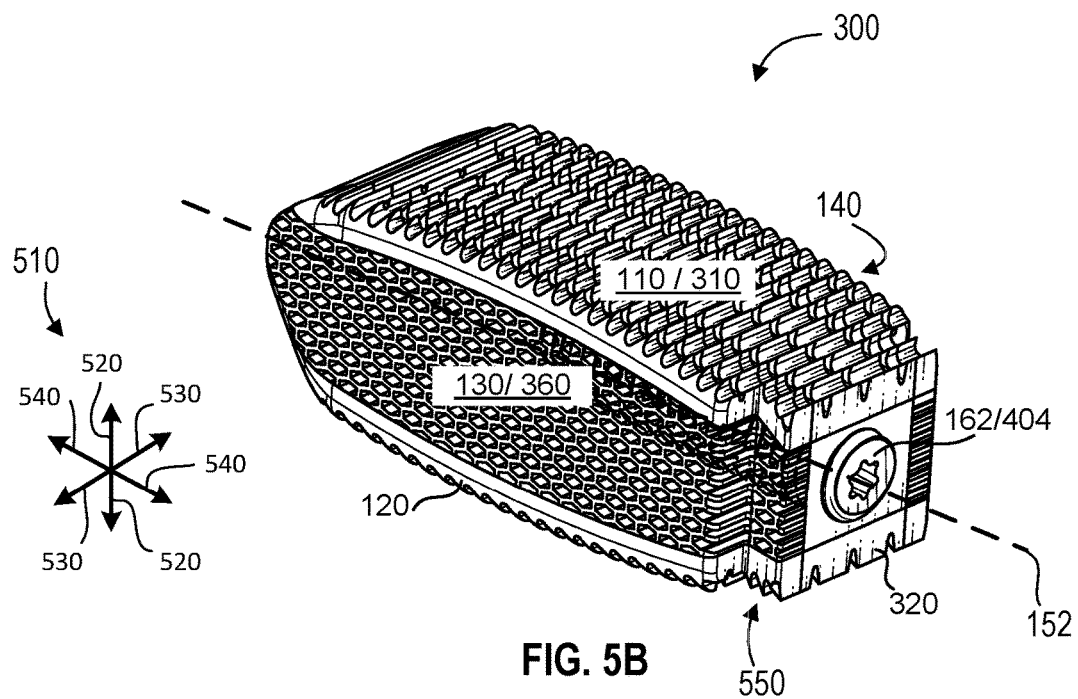
FIG. 5B is perspective view of the expandable intervertebral implant 300 of FIG. 3A in an expanded configuration with the screw member of FIG. 4A within the expanded configuration 300.

FIG. 5B is perspective view of the expandable intervertebral implant 300 of FIG. 3A in an expanded configuration with the screw member 400 of FIG. 4A within the expanded configuration 300.

Referring now to FIGS. 5A and 5B together, operation of the expandable intervertebral implant 300 is described. During a surgical procedure, a surgeon may install the expandable intervertebral implant 300 through a cannula for a MIS procedure or using another instrument for an invasive procedure. As the expandable intervertebral implant 300 is inserted into the body of the patient, the expandable intervertebral implant 300 is in a collapsed configuration. Once in the desired position, the driver 162 of the expansion mechanism 160 may be activated to transition the expandable intervertebral implant 300 from a collapsed configuration to an expanded configuration.

In FIG. 5A, the expandable intervertebral implant 300 is in a collapsed configuration. FIG. 5A illustrates how the screw member 400 can be inserted into the opening 150 to cause the expandable intervertebral implant to transition from a collapsed configuration to a partially expanded configuration or fully expanded configuration. The screw member 400 may be passed through a cannula or inserted into the opening 150 directly by a user. In one embodiment, a cross-section for the tapered end 416 is smaller than, or not larger than, a height and width of the opening 150.

FIG. 5B illustrates the expandable intervertebral implant 300 in an expanded configuration. As used herein, a "collapsed configuration" refers to an arrangement of an upper plate 110, a lower plate 120, a first lattice 130, a second lattice 140, an opening 150, and an expansion mechanism 160 such that the apparatus or assembly has its smallest height. In certain embodiments, the expandable intervertebral implant 300 is configured such that the upper plate 110 engages the lower plate 112 such that the upper plate 110 is as close as possible to the lower plate 112 in the collapsed configuration. As used herein, an "expanded configuration" refers to an arrangement of an upper plate 110, a lower plate 120, a first lattice 130, a second lattice 140, an opening 150, and an expansion mechanism 160 such that the apparatus or assembly has its greatest height and/or width. In certain embodiments, the expandable intervertebral implant 300 is configured such that the upper plate 110 moves as far away from the lower plate 120 as possible in the expanded configuration.

FIG. 5B illustrates a three-dimensional axis 510. The three-dimensional axis 510 includes a cephalad-caudal axis 520, a medial-lateral axis 530, and an anterior-posterior axis 540. The three-dimensional axis 510 is used to identify how an expandable intervertebral implant transitions from a collapsed configuration to an expanded configuration, including a partially expanded configuration.

In one embodiment, insertion of the expansion mechanism 160 causes the expansion of one or more sides/walls of the expandable intervertebral implant. In another embodiment, the expansion mechanism 160 may be integrated with, connected, or coupled to the expandable intervertebral implant such that activation of the expansion mechanism 160 causes the expansion of the expandable intervertebral implant. Similarly, de-activation, disengagement, or removal of the expansion mechanism 160 can cause contraction of the expandable intervertebral implant, transition of the expandable intervertebral implant towards a collapsed configuration. In yet another embodiment, lattices or meshes of the expandable intervertebral implant can be configured such that the expandable intervertebral implant retains an expanded configuration or partial expanded configuration in response to de-activation, disengagement, or removal of the expansion mechanism 160.

In certain embodiments, activation of the expansion mechanism 160 can include insertion of the expansion mechanism 160 into the opening 150. In such an embodiment, the driver 162 may include a force pressing the expansion mechanism 160 into the opening 150. In the illustrated embodiment, the expansion mechanism 160 is embodied as a screw member 400 and the driver 162 is the drive recess 502. The expansion mechanism 160 may be activated by inserting the distal end 408 of the screw member 400 into the opening 150 and arranging the threads 410 such that they engage the internal threads 154 and then engaging the drive recess 502 and rotating the screw member 400 about its longitudinal axis 414 in a direction that causes the screw member 400 to move further into the opening 150. Engagement of the drive recess 502 and rotating the screw member 400 about its longitudinal axis 414 is referred to herein as activation of the driver 162, for this embodiment. As the screw member 400 moves further into the opening 150, the opening 150 enlarges to accept the screw member 400.

In one embodiment, an amount of expansion provided by the expansion mechanism 160, such as the screw member 400, may be determined, at least in part, by a cross-sectional diameter of the screw member 400. The greater the cross-sectional diameter of the screw member 400, the greater the amount of expansion. Furthermore, the direction(s) of expansion may depend on the embodiment of the expandable intervertebral implant used.

For example, if the expandable intervertebral implant is embodied as the expandable intervertebral implant 200 of FIGS. 2A,2B having a first lattice 130, a second lattice 140, a solid upper plate 110, a solid lower plate 120, insertion of the screw member 400 into the opening 150 deforms the first lattice 130 and the second lattice 140. The first lattice 130 and the second lattice 140 deform because the cross-sectional diameter of the screw member 400 is greater than a height of the opening 150. Insertion of the screw member 400 and deformation of the first lattice 130 and the second lattice 140 expands the upper plate 110 and the lower plate 120 away from each other along the cephalad-caudal axis 520. This expansion may cause the upper plate 110 to engage a superior vertebral body (not shown) and the lower plate 120 to engage an inferior vertebral body (not shown). Activation of the driver 162 separates the upper plate 110 from the lower plate 120 by deforming the first lattice 130 and the second lattice 140.

If the expandable intervertebral implant is embodied as the expandable intervertebral implant 300 of FIGS. 3A-3D and 5A, 5B having a first wall 350 with a first mesh 360, a second wall 352 with a second mesh 362, an upper plate 110 that includes an upper mesh 370, and a lower plate 120 having lower mesh 380, insertion of the screw member 400 into the opening 150 deforms the first mesh 360, the second mesh 362, the upper mesh 370, and the lower mesh 380. In such an embodiment, the screw member 400 can have a cross-sectional diameter that is greater than a height and/or a width of the opening 150. The first mesh 360, the second mesh 362, the upper mesh 370, and the lower mesh 380 deform, at least in part, because the cross-sectional diameter of the screw member 400 is greater than the height and/or the width of the opening 150.

Insertion of the screw member 400 and activation of the driver 162 (head 404 and drive recess 502) expands the upper plate 110 and the lower plate 120 away from each other along the cephalad-caudal axis 520 by expanding the first mesh 360 and the second mesh 362 and moves the first wall 350 and the second wall 352 away from each other along a medial-lateral axis 530 by expanding the upper mesh 370 and the lower mesh 380. This expansion may cause the upper plate 110 to engage a superior vertebral body (not shown) and the lower plate 120 to engage an inferior vertebral body (not shown) and the first wall 350 and the second wall 352 to separate to fill more space between the superior vertebral body and the inferior vertebral body.

In one embodiment, activation of the driver 162 can include rotating a screw member 400 about its longitudinal axis 414 moves the screw member 400 deeper into the opening 150 such that the driver 162 expands the first mesh 360, the second mesh 362, the upper mesh 370, and the lower mesh 380.

In one embodiment, the expandable intervertebral implant may be embodied similar to the expandable intervertebral implant 300 illustrated in FIGS. 3A-3D and 5A, 5B. In such an embodiment, the expandable intervertebral implant can include a first lattice 130 that connected a first upper side 112 of the upper plate 110 to a first lower side 122 of the lower plate 120. The expandable intervertebral implant can also include a second lattice 140 that connected a second upper side 114 of the upper plate 110 to a second lower side 124 of the lower plate 120. The expandable intervertebral implant can also include an upper lattice 310 in the upper plate 110 and a lower lattice 320 in the lower plate 120. The expandable intervertebral implant can include an opening 150 with internal threads 154 about a longitudinal axis 152 between the upper plate 110, the lower plate 120, the first lattice 130 and the second lattice 140.

In such an embodiment, insertion of a screw member 400 into the opening 150 deforms the first lattice 130, the second lattice 140, the upper lattice 310, and the lower lattice 320. In such an embodiment, the screw member 400 can have a cross-sectional diameter that is greater than a height and/or a width of the opening 150. The first lattice 130, the second lattice 140, the upper lattice 310, and the lower lattice 320 deform, at least in part, because the cross-sectional diameter of the screw member 400 is greater than the height and/or the width of the opening 150.

Insertion of the screw member 400 and activation of the driver 162 (head 404 and drive recess 502) separates the upper plate 110 from the lower plate 120 by deforming the first lattice 130 and the second lattice 140 and separates the first lattice 130 and the second lattice 140 by deforming the upper lattice 310 and the lower lattice 320. In one particular embodiment, the driver 162 is configured to rotate the screw member 400 about the longitudinal axis 414 and such rotation moves the screw member 400 within the opening 150 and expands the expandable intervertebral implant along the cephalad-caudal axis 520 and the medial-lateral axis 530 to a target expanded configuration. This expansion can cause the upper plate 110 to engage a superior vertebral body (not shown) and the lower plate 120 to engage an inferior vertebral body (not shown) and the first lattice 130 and the second lattice 140 to separate to fill more space between the superior vertebral body and the inferior vertebral body. In such an embodiment, activation of the expansion mechanism 160 by the driver 162 expands the upper plate 110 and the lower plate 120 away from each other along the cephalad-caudal axis 520 and moves the first lattice 130 and the second lattice 140 away from each other along a medial-lateral axis 530 by deforming the first lattice 130, the second lattice 140, the upper lattice 310, and the lower lattice 320.

Figure 5C:
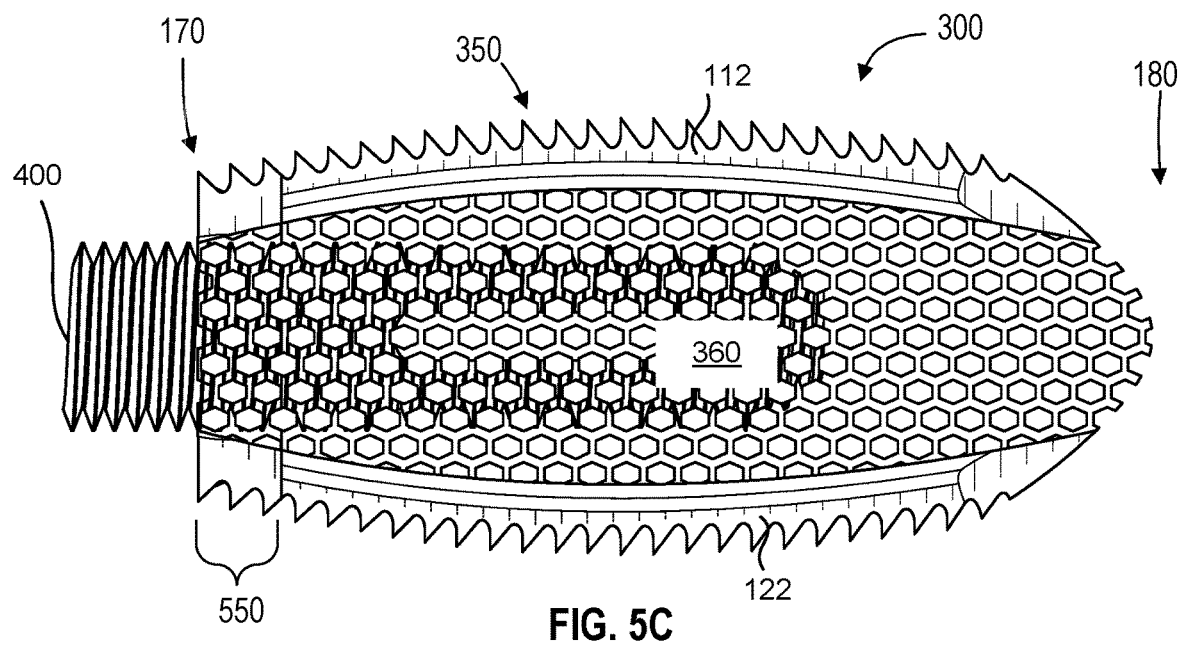
FIG. 5C is a side elevation view of the expandable intervertebral implant 300 of FIG. 3A in an expanded configuration.
Figure 5D:
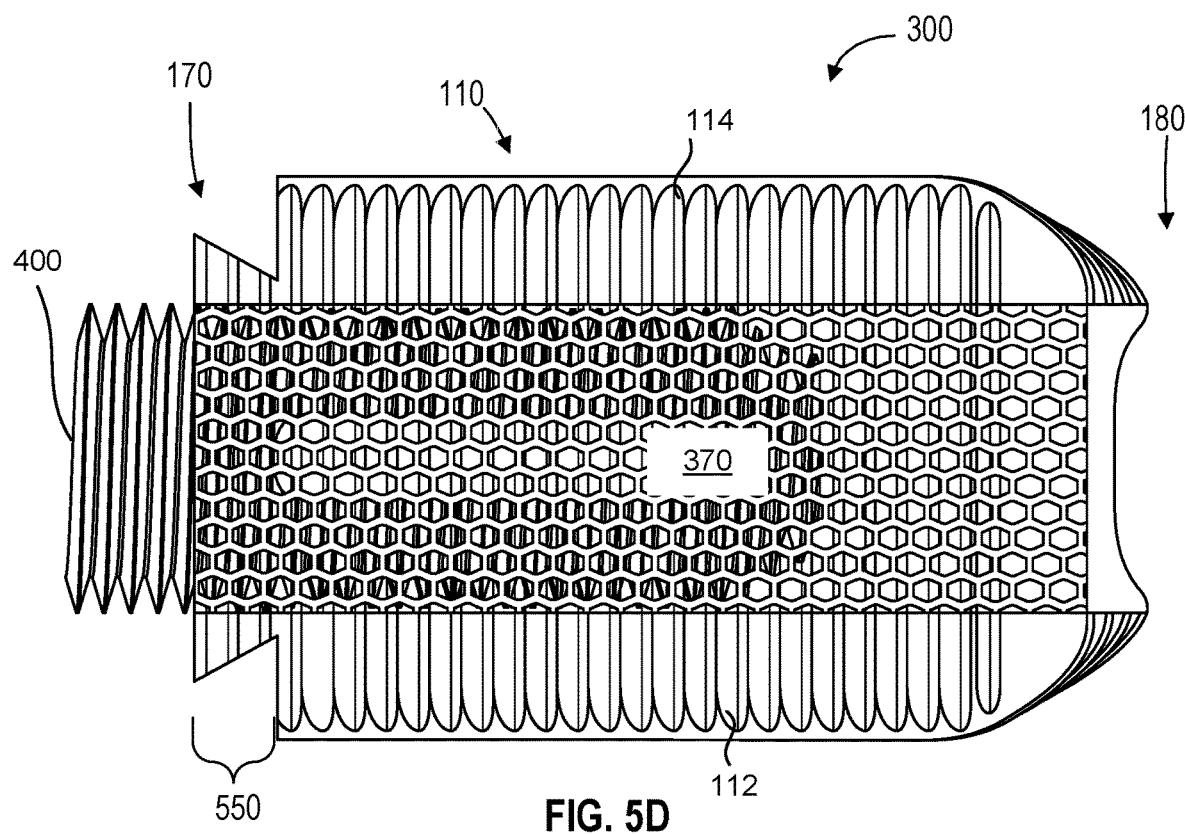
FIG. 5D is a plan view of the expandable intervertebral implant 300 of FIG. 3A in an expanded configuration.

FIG. 5C is a side elevation view of the expandable intervertebral implant 300 of FIG. 3A in an expanded configuration. FIG. 5D is a plan view of the expandable intervertebral implant 300 of FIG. 3A in an expanded configuration. FIGS. 5C and 5D illustrate one embodiment of an expandable intervertebral implant with the expansion mechanism 160 activated such that the expandable intervertebral implant is in an expanded configuration.

In the illustrated embodiment, the expansion mechanism 160 comprises a screw member 400 inserted within the opening 150. FIG. 5C illustrates that the first lattice 130 is expanded, deformed, or stretched along the cephalad-caudal axis 520. Similarly, the second lattice 140 (not shown in FIG. 5C) is expanded, deformed, or stretched along the cephalad-caudal axis 520. FIG. 5D illustrates that the upper lattice 310 is expanded, deformed, or stretched along the medial-lateral axis 530. Similarly, the lower lattice 320 (not shown in FIG. 5D) is expanded, deformed, or stretched along the medial-lateral axis 530.

FIGS. 5C and 5D illustrate that the expandable intervertebral implant 300 includes a proximal end 170 and a distal end 180. In one embodiment, the expandable intervertebral implant 300 includes a first wall 350 having a first mesh 360 and a second wall 352 having a second mesh 362. FIG. 5C illustrates that the first mesh 360 spans the first wall 350 from the first upper side 112 to the first lower side 122 and from the proximal end 170 to the distal end 180. Because the first wall 350 is symmetrical to the second wall 352, those of skill in the art will recognize that the second mesh 362 of the expandable intervertebral implant 300 spans the second wall 352 from the second upper side 114 to the second lower side 124 and from the proximal end 170 to the distal end 180.

In one embodiment, the expandable intervertebral implant 300 includes an upper plate 110 having an upper mesh 370 and a lower plate 120 having a lower mesh 380. FIG. 5D illustrates that the upper mesh 370 spans the upper plate 110 from the first upper side 112 to the second upper side 114 and from the proximal end 170 to the distal end 180. Because the lower plate 120 is symmetrical to the upper plate 110, those of skill in the art will recognize that the lower mesh 380 of the expandable intervertebral implant 300 spans the lower plate 120 from the first lower side 122 to the second lower side 124 and from the proximal end 170 to the distal end 180.

In certain embodiments, the expandable intervertebral implant 300 includes an inserter attachment feature 550. The inserter attachment feature 550 serves to connect the expandable intervertebral implant 300 to an insertion tool (not shown) during an operation. For example, the inserter attachment feature 550 may be configured to removably attach the expandable intervertebral implant 300 to part of an insertion tool. FIGS. 5C and 5D illustrate that the inserter attachment feature 550 may have a dove-tail shape (FIG. 5D) that enables a clamp, jaws, fork, or similar part of an insertion tool to removably engage with the expandable intervertebral implant 300 when the expandable intervertebral implant 300 is being positioned during an operation. Those of skill in the art will appreciate the different insertion tools that can removably engage the plurality of teeth 330 and provide a counter-torque when an expansion mechanism 160 is activated (such as rotation of a screw member 400).

Advantageously, as illustrated in FIGS. 5C and 5D, a lattice, mesh, or other pattern of an upper plate 110, lower plate 120, first wall 350, second wall 352, first lattice 130, or second lattice 140 may extend to include the structures of the inserter attachment feature 550. In this manner, as the expandable intervertebral implant 300 expands along a cephalad-caudal axis 520 and/or medial-lateral axis 530, components of the inserter attachment feature 550 do not impede the expansion.

Figure 5E:
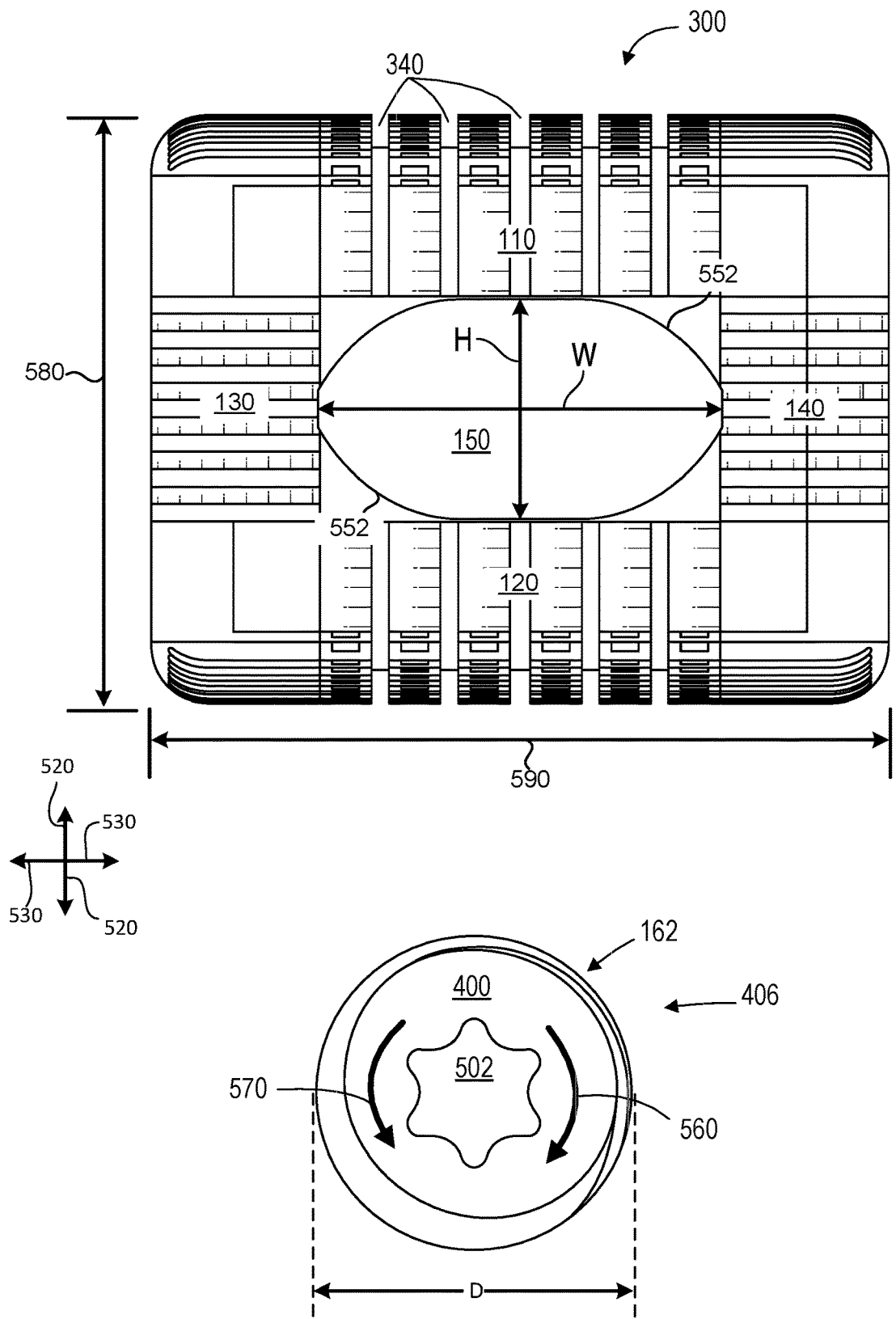
FIG. 5E illustrates a proximal end view of the expandable intervertebral implant 300 of FIG. 5A in a collapsed configuration and a screw member.
Figure 5F:
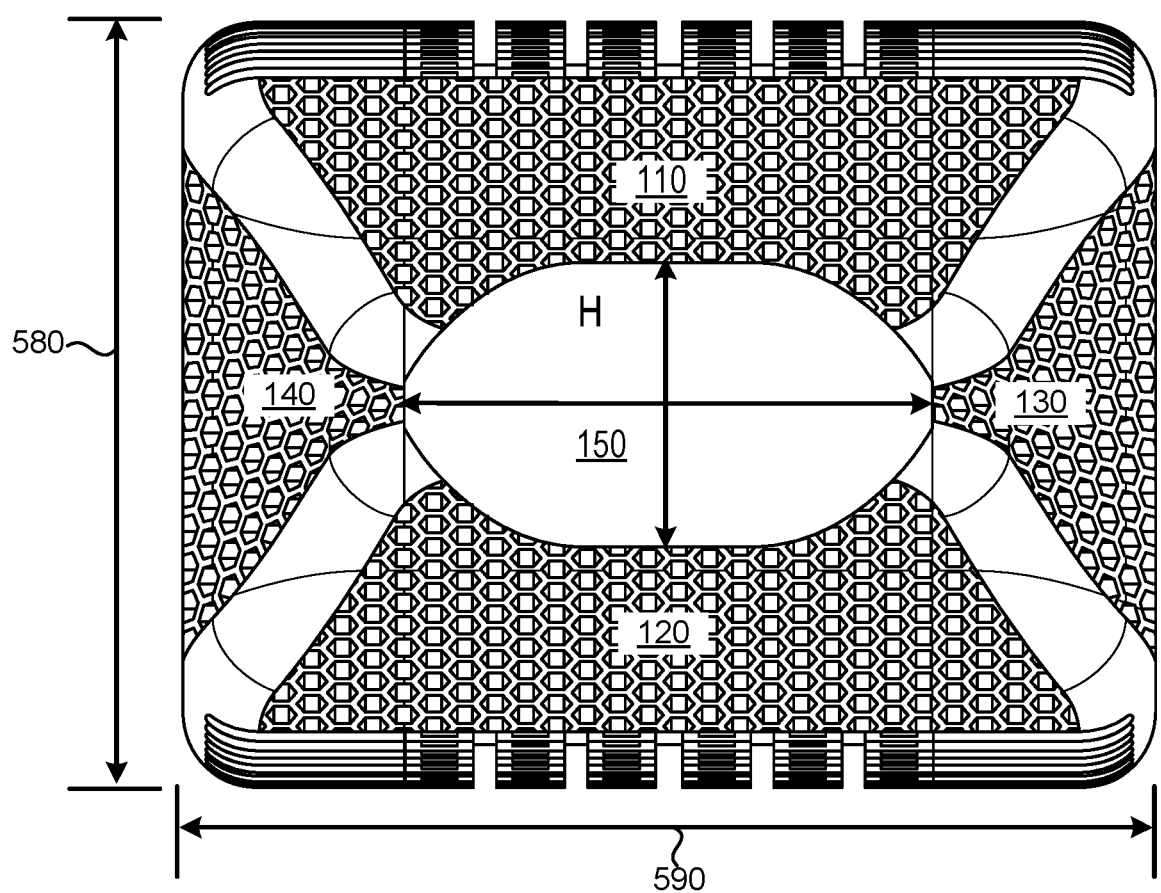
FIG. 5F illustrates a distal end view of the expandable intervertebral implant 300 of FIG. 5A in a collapsed configuration and a screw member.
Figure 5F:
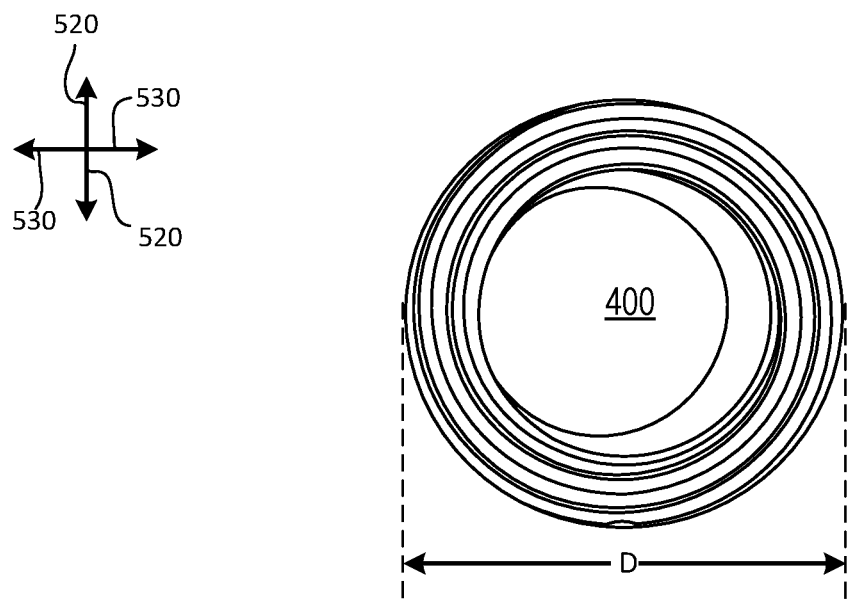

FIG. 5E illustrates a proximal end view of the expandable intervertebral implant 300 of FIG. 5A in a collapsed configuration and a proximal end 406 of a screw member 400. FIG. 5F illustrates a distal end view of the expandable intervertebral implant 300 of FIG. 5A in a collapsed configuration and a distal end 408 of a screw member 400.

Referring now to FIGS. 5E and 5F, in one embodiment, the opening 150 includes a height H and a width W. The opening 150 may have an ovoid cross-section 552. The ovoid cross-section 552 includes a height H that is different from a width W of the ovoid cross-section 552. In one embodiment, the height H is shorter than the width W. Alternatively, or in another embodiment, the opening 150 may have an elliptical cross-section having a height H that is smaller than a width W.

The size and shape of the opening 150 and the cross-sectional diameter of the screw member 400 (including the threads 410) impact how much the expandable intervertebral implant 300 expands when the screw member 400 is inserted into the opening 150. In one embodiment, the screw member 400 has a cross-sectional diameter D greater than height H of the opening 150. In this manner, as the screw member 400 is inserted in the opening, the lattice, mesh, and/or pattern of pores/openings in the upper plate 110 (or upper mesh 370), lower plate 120 (or lower mesh 380), and first lattice 130 and second lattice 140 (or first wall 350 and second wall 352) enable the opening 150 to enlarge to accept the screw member 400. In certain embodiments, the cross-sectional diameter D of the screw member 400 is greater than width W of the opening 150. In such an embodiment, insertion of the screw member 400 causes the opening 150 to widen beyond width W.

A drive member is configured to engage the drive recess 502 and rotate the screw member 400 in direction 560 or in direction 570. In one embodiment, rotation of the screw member 400 in direction 560 moves the screw member 400 deeper into the opening 150 and rotation of the screw member 400 in direction 570 moves the screw member 400 out of the opening 150, extracts the screw member 400. In one embodiment, activation of a driver 162 includes engaging the drive recess 502 and rotating the screw member 400 in the direction that moves the screw member 400 into the opening 150 and de-activation of the driver 162 includes engaging the drive recess 502 and rotating the screw member 400 in the direction that removes the screw member 400 from the opening 150.

FIGS. 5E and 5F illustrate the expandable intervertebral implant in a collapsed configuration with a height 580 and a width 590 which are the respective height and width of the expandable intervertebral implant 300 prior to activation of the driver 162 of the expansion mechanism 160.

Figure 5G:
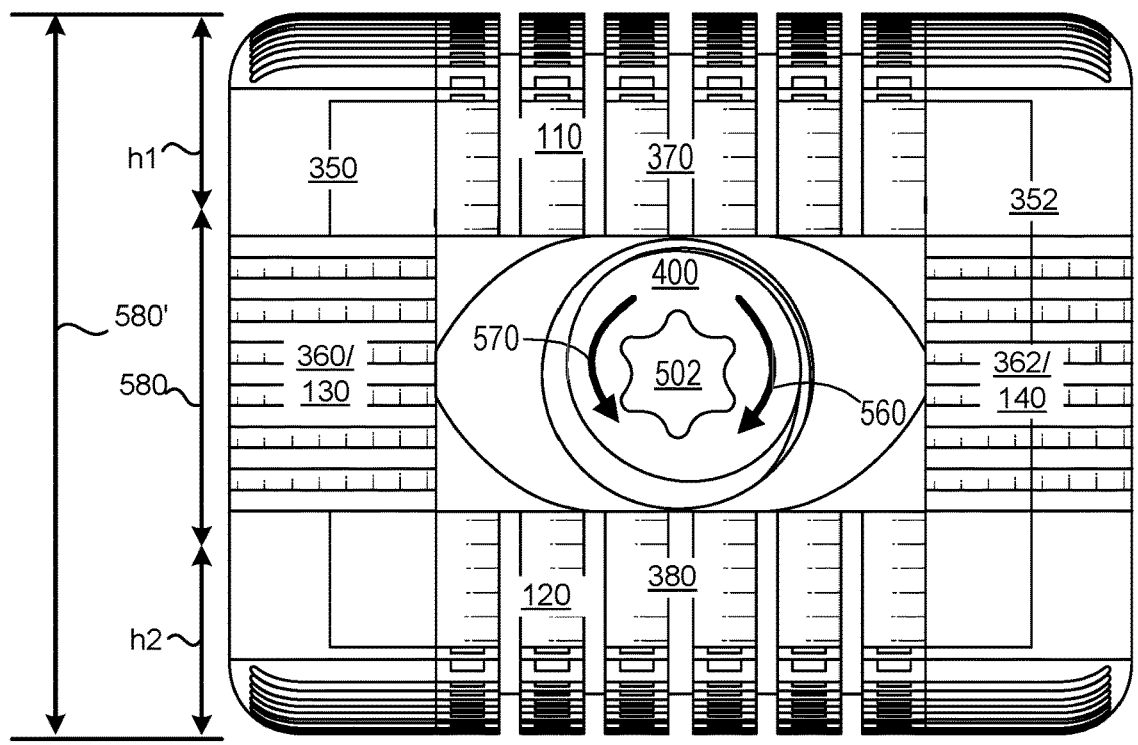
FIG. 5G illustrates a proximal end view of the expandable intervertebral implant 300 of FIG. 5A in an expanded configuration with a screw member.
Figure 5H:
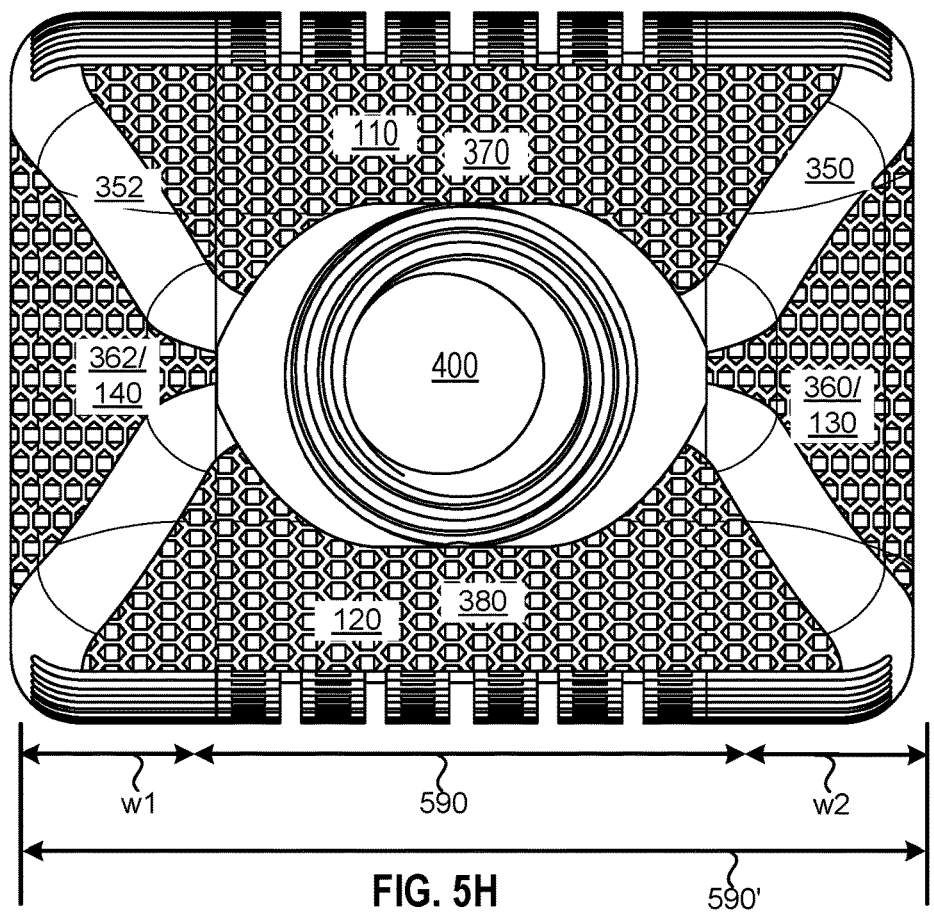
FIG. 5H illustrates a distal end view of the expandable intervertebral implant 300 of FIG. 5A in an expanded configuration with a screw member.

FIG. 5G illustrates a proximal end view of the expandable intervertebral implant 300 of FIG. 5A in an expanded configuration with a screw member 400. FIG. 5H illustrates a distal end view of the expandable intervertebral implant 300 of FIG. 5A in an expanded configuration with a screw member 400. In the expanded configuration, the height 580 has become a greater height 580' and the width 590 has become a greater width 590'. FIGS. 5G and 5H illustrate that the expandable intervertebral implant 300 has expanded along both the cephalad-caudal axis 520 and the medial-lateral axis 530 to a target expanded configuration. The target expanded configuration may have the increased height 580' and increased width 590'.

In certain embodiments, the expandable intervertebral implant 300 can include a first mesh 360 (of first wall 350), a second mesh 362 (of second wall 352), an upper mesh 370 and a lower mesh 380. The first mesh 360 and second mesh 362 may each have a particular pattern of pores or openings in the mesh, referred to herein as a first pattern. In addition, the opening 150 may comprise an elliptical cross-section with a predetermined height H. In such an embodiment, the first pattern and height of the elliptical cross-section of the opening 150 may be each selected such that activation of the driver 162 of the expansion mechanism 160 causes a pre-determined increase in distance (ΔH=height 580'−height 580) between the upper plate 110 and the lower a plate 120.

In addition, or alternatively, the upper mesh 370 and lower mesh 380 may each include a second pattern. The second pattern may be the same as the first pattern or the first pattern and the second pattern may each be different. The first pattern and the second pattern may each be selected such that activation of the driver 162 of the expansion mechanism 160 causes a first predetermined increase in a distance, such as (ΔH=height 580'−height 580, or h1+h2), between the upper plate 110 and the lower plate 120 that differs from a second predetermined increase in a distance, such as (ΔW=width 590'−width 590, or w1+w2), between the first wall 350 and the second wall 352. By using a different pattern for the upper lattice 310 and lower lattice 320 from a pattern used for the first lattice 130 and second lattice 140 an amount of expansion along a cephalad-caudal axis 520 and a medial-lateral axis 530 can each be independently managed or determined.

In certain embodiments, a range of expandable intervertebral implants may be made available to a surgeon. The range of expandable intervertebral implants may include a plurality of variations among the size and/or shape of the opening 150, pattern(s) for the lattice and/or mesh of the lattices, walls, or plates, different expansion mechanisms 160, and the like. For example, different patterns for opposite sides of the expandable intervertebral implant may be used in the range of expandable intervertebral implants which each provide a different amount of expansion when installed.

If a range of implants may be used for a given procedure, the plurality of variations among the size and/or shape of the opening 150, pattern(s) for the lattice and/or mesh of the lattices, walls, or plates, different expansion mechanisms 160 may facilitate pre-operative selection of the optimal implant(s). More particularly, a suitable size, shape, ratio of collapsed height and/or width to expanded height and/or width, type of expansion mechanism 160, and/or other hardware may be pre-operatively selected. In this manner, the surgeon may choose an expandable intervertebral implant that may provide an optimal outcome for the patient.

In one embodiment, that includes a single pre-operatively selected expandable intervertebral implant or an expanded configuration selected from a range of implants, the first lattice 130 and the second lattice 140 may each have a pre-selected first pattern, size of the opening 150, and/or cross-sectional diameter of the screw member 400 such that rotation of the screw member 400 about the longitudinal axis moves the screw member 400 within the opening 150 and expands the expandable intervertebral implant 100/300 along a cephalad-caudal axis 520 and along a medial-lateral axis 530 to a target expanded configuration.

Alternatively, or in addition, a single expandable intervertebral implant may be available and the expansion mechanism 160 may include a set of screw members 400. Each member of the set of screw members 400 may have a different cross-sectional diameter. In one embodiment, a surgeon may use a plurality of screw member 400 from the set of screw members 400 to expand the expandable intervertebral implant. For example, the surgeon may start with a screw member 400 having a smaller diameter, insert this screw member 400, remove the smaller diameter screw member 400, and then insert progressively larger diameter screw members 400 until an optimal level of expansion is achieved.

Figure 6A:
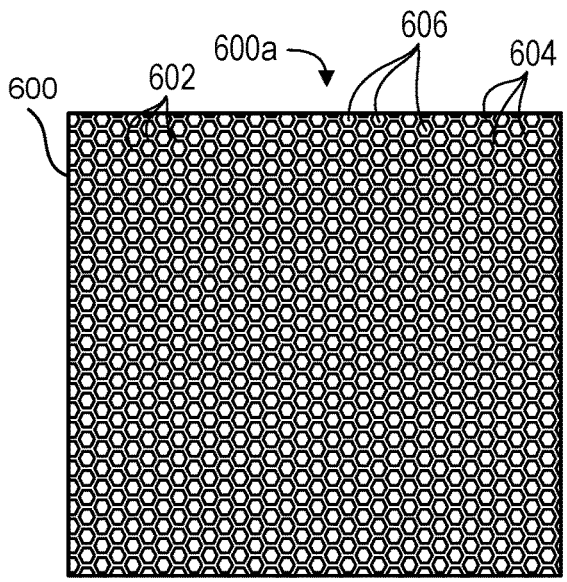
FIGS. 6A-6F illustrates different patterns that can be used in various embodiments of the present disclosure.
Figure 6B:
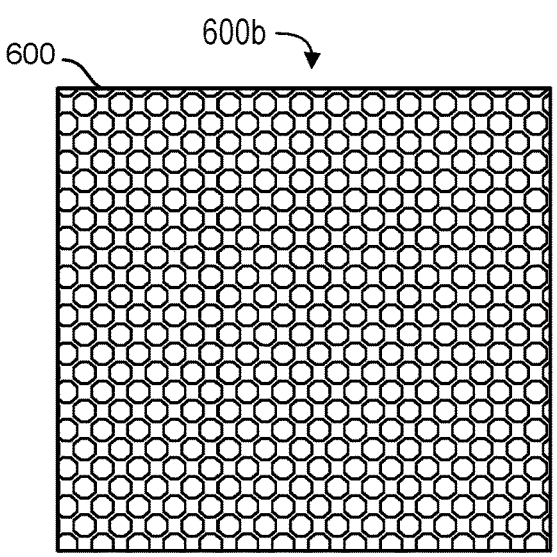
Figure 6C:
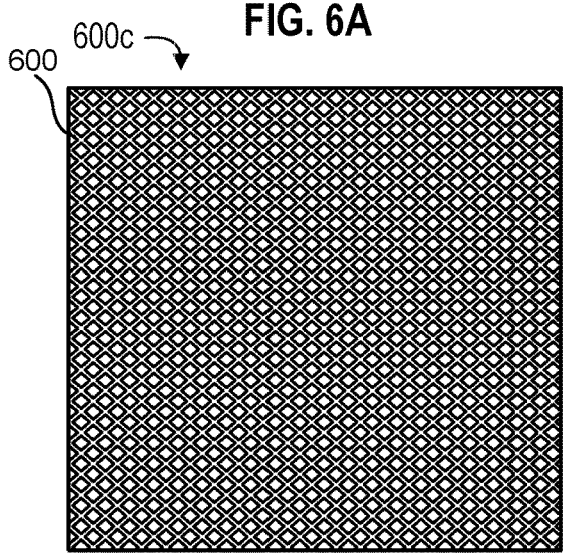
Figure 6D:
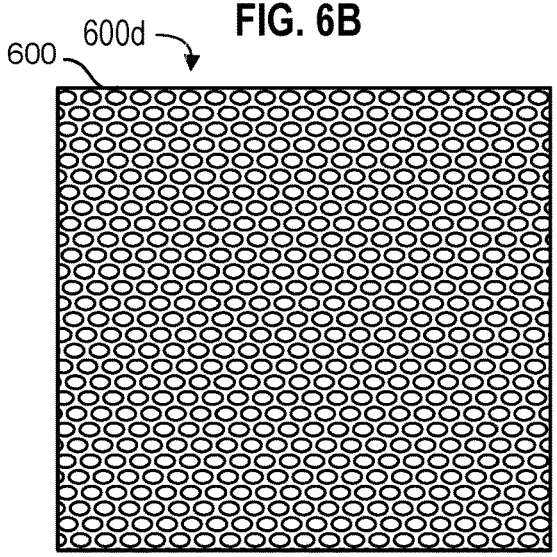
Figure 6E:
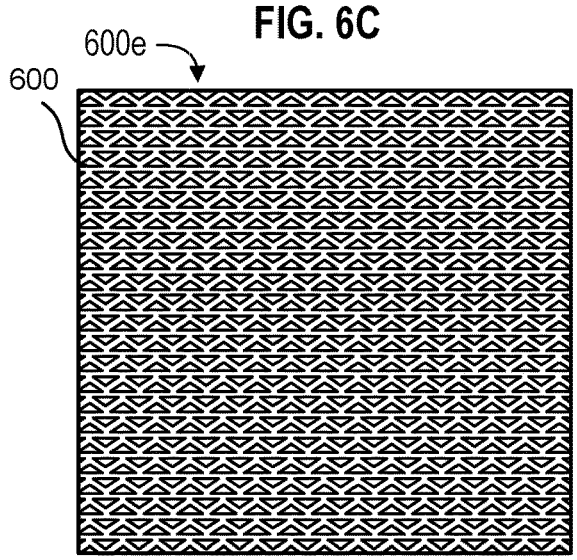

FIGS. 6A-6F illustrates different patterns that can be used in embodiments of the present disclosure. FIG. 6A illustrates a pattern 600 created by a uniform spacing of geometric shapes 602. In certain embodiments, the pattern 600 may be formed from one or more other geometric shapes including polygons, and shapes formed from curves such as circles, ovals, ovoids, ellipse, or the like. In certain embodiments, the edges 604 are configured to break or fail as the expandable intervertebral implant expands. This breakage may increase structural strength of components of the expandable intervertebral implant that include these edges 604.

In FIG. 6A, the geometric shapes 602 are hexagons. The geometric shapes 602 are formed by edges 604 that define pores or openings 606 in the pattern 600. The pores 606 facilitate expansion of the structure having the pattern. The pores 606 may facilitate bone growth through the expandable intervertebral implant as part of a recovery process once the expandable intervertebral implant is installed in a patient.

As an expandable intervertebral implant expands the geometric shapes 602 deform and stretch. The size, shape, and distribution of the pores 606 may be predetermined such that the structure having the pattern will expand to a desired or target distance.

In the pattern 600a of FIG. 6A, the geometric shapes 602 are hexagons. In the pattern 600b of FIG. 6B, the geometric shapes 602 are octagons. In the pattern 600c of FIG. 6C, the geometric shapes 602 are diamonds. In the pattern 600d of FIG. 6D, the geometric shapes 602 are ovals. In the pattern 600e of FIG. 6E, the geometric shapes 602 are triangles. In the pattern 600f of FIG. 6D, the geometric shapes 602 are quadrilaterals, such as for example trapezoids.

Figure 6F:
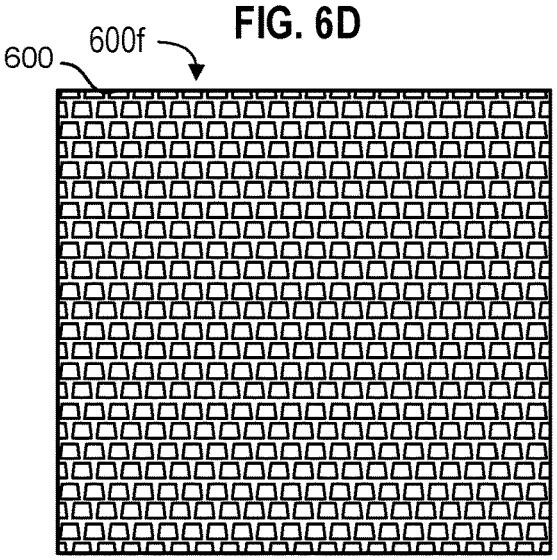
Figure 7A:
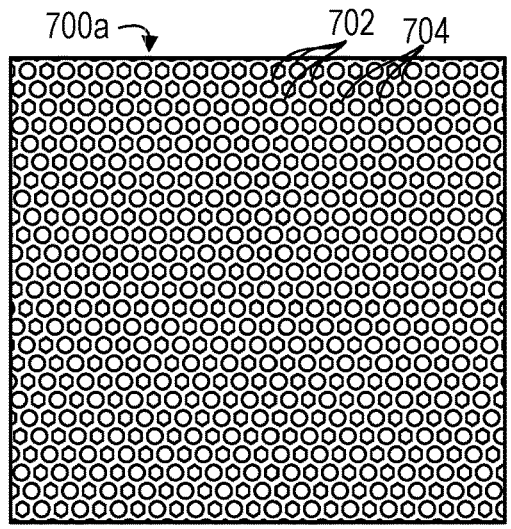
FIGS. 7A-7C illustrates different patterns that can be used in various embodiments of the present disclosure.
Figure 7B:
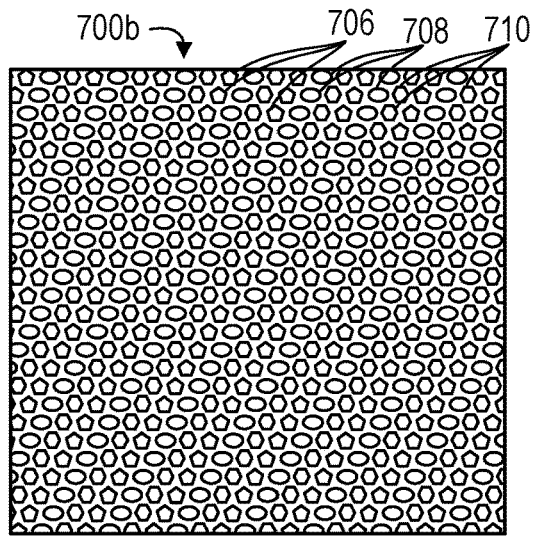
Figure 7C:
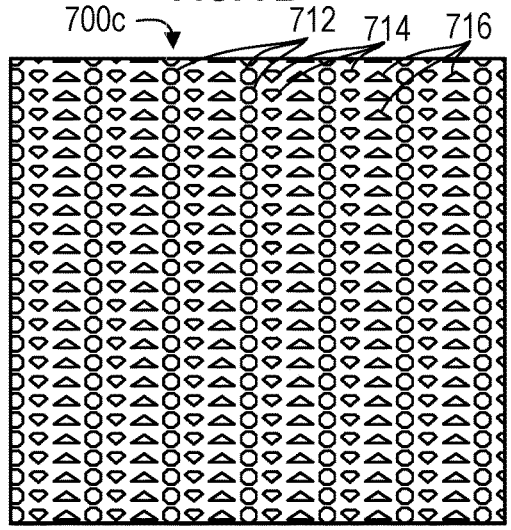

FIGS. 7A-6F illustrates different patterns 700a-c that can be used in various embodiments of the present disclosure. In certain embodiments, the patterns 700a-c can include one geometric shape, two geometric shapes, or a combination three or more geometric shapes. The shapes and/or designs that make up the pattern are a set of geometric shapes. Each of the shapes of the pattern can include a pore or opening such that the pattern includes a distributed set of one or more geometric shapes comprising a set of pores.

For example, pattern 700a illustrates a pattern for embodiments in which the pattern includes two geometric shapes. In the illustrated embodiment, the pattern 700a includes a repeated and evenly distributed set of circles 702 and hexagons 704.

Pattern 700b illustrates a pattern for embodiments in which the pattern includes three geometric shapes. In the illustrated embodiment, the pattern 700a includes a repeated and evenly distributed set of pentagons 706, ovals 708, and hexagons 710.

Pattern 700c illustrates a pattern for embodiments in which the pattern includes three geometric shapes. In the illustrated embodiment, the pattern 700a includes a repeated and evenly distributed set of octagons 712, diamonds 714, and triangles 716.

Referring generally to FIGS. 6A-6F and 7A-7C, those of skill in the art recognize that the pattern used in the mesh or lattices of the present disclosure can be of any shape, design or pattern. The examples disclosed herein, are examples of a few of the possible patterns that can be used. In addition, the mesh and/or lattices that include a pattern can be made from the same material as other structures of the expandable intervertebral implant. For example, each of these structures can be made from titanium or a titanium alloy. For example, in one embodiment, the upper plate 110, the lower plate 120, the first lattice 130, and the second lattice 140 can be made from titanium or a titanium alloy.

Alternatively, or in addition, meshes and/or lattices that include a pattern can be made from a different material as other structures of the expandable intervertebral implant. In certain embodiments, the pattern, the size of the pores in the pattern the positioning and distribution of geometric shapes or other designs that create the pattern and the thickness of edges 604 for the pattern can each be selected or designed to achieve a desired increase in distance between plates, walls, or lattices of an expandable intervertebral implant.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. An expandable intervertebral implant comprising:
an upper plate comprising a first upper side and a second upper side;
a lower plate comprising a first lower side and a second lower side;
a first lattice that connects the first upper side of the upper plate to the first lower side of the lower plate;
a second lattice that connects the second upper side of the upper plate to the second lower side of the lower plate;

an opening having a longitudinal axis between the upper plate, the lower plate, the first lattice, and the second lattice and comprising internal threads about the longitudinal axis; and an expansion mechanism comprising a driver and a screw member comprising a shank comprising threads that engage the internal threads within the opening, the screw member having a diameter selected such that rotation of the screw member about the longitudinal axis, by activation of the driver, moves the upper plate and the lower plate away from each other by deforming the first lattice and the second lattice;

wherein the driver of the expansion mechanism comprises a head of the screw member connected to a proximal end of the shank; and wherein the screw member comprises a tapered end connected to a distal end of the shank and the screw member comprises a cross-sectional diameter greater than a height of the opening.

2. The expandable intervertebral implant of claim 1, wherein the cross-sectional diameter of the screw member is greater than a width of the opening.

3. The expandable intervertebral implant of claim 1, wherein the expansion mechanism comprises a set of screw members each comprising a shank comprising threads that engage the internal threads within the opening, each screw member of the set of screw members having a different cross-sectional diameter.

4. The expandable intervertebral implant of claim 1, wherein the upper plate comprises an upper lattice and the lower plate comprises a lower lattice and wherein the expansion mechanism is configured such that activation of the expansion mechanism by the driver expands the upper plate and the lower plate away from each other along the cephalad-caudal axis and moves the first lattice and the second lattice away from each other along a medial-lateral axis by deforming the first lattice, the second lattice, the upper lattice, and the lower lattice.

5. The expandable intervertebral implant of claim 1, wherein the opening comprises an ovoid cross-section that comprises a height that is different from a width of the ovoid cross-section.

6. The expandable intervertebral implant of claim 1, wherein the first lattice and the second lattice are made of metal.

7. The expandable intervertebral implant of claim 1, wherein the first lattice comprises a first pattern and the second lattice comprises a second pattern wherein the first pattern is generally the same as the second pattern.

8. The expandable intervertebral implant of claim 7, wherein the first pattern and the second pattern each comprises one or more of a set of geometric shapes comprising pores.

9. An expandable intervertebral implant comprising:
an upper plate comprising an upper mesh, a first upper side, and a second upper side;
a lower plate comprising a lower mesh, a first lower side, and a second lower side;
a first wall that connects the first upper side of the upper plate to the first lower side of the lower plate, the first wall comprising a first mesh;
a second wall that connects the second upper side of the upper plate to the second lower side of the lower plate, the second wall comprising a second mesh;

an opening having a longitudinal axis between the upper plate, the lower plate, the first wall, and the second wall and comprising internal threads about the longitudinal axis; and an expansion mechanism comprising a driver and a screw member comprising a shank comprising threads that engage the internal threads within the opening, the screw member having a diameter selected such that rotation of the screw member about the longitudinal axis, by activation of the driver, moves the upper plate and the lower plate away from each other along a cephalad-caudal axis-by expanding the first mesh and the second mesh and moves the first wall and the second wall away from each other along a medial-lateral axis by expanding the upper mesh and the lower mesh;

wherein the driver of the expansion mechanism comprises a head of the screw member connected to a proximal end of the shank; and wherein the screw member comprises a tapered end connected to a distal end of the shank and the screw member comprises a cross-sectional diameter greater than a height of the opening.

10. The expandable intervertebral implant of claim 9, wherein the opening comprises an elliptical cross-section that comprises a height that is smaller than a width of the elliptical cross-section.

11. The expandable intervertebral implant of claim 10, wherein the first mesh and the second mesh each comprise a first pattern and wherein the first pattern and the height of the elliptical cross-section of the opening are each selected such that activation of the driver of the expansion mechanism causes a predetermined increase in distance between the upper plate and the lower plate.

12. The expandable intervertebral implant of claim 9, further comprising:
a proximal end;
a distal end;
wherein the first mesh spans the first wall from the first upper side to the first lower side and from the proximal end to the distal end;
wherein the second mesh spans the second wall from the second upper side to the second lower side and from the proximal end to the distal end;
wherein the upper mesh spans the upper plate from the first upper side to the second upper side and from the proximal end to the distal end; and
wherein the lower mesh spans the lower plate from the first lower side to the second lower side and from the proximal end to the distal end.

13. An expandable intervertebral implant comprising:
an upper plate comprising an upper lattice, a first upper side, and a second upper side;
a lower plate comprising a lower lattice, a first lower side and a second lower side;
a first lattice that connects the first upper side of the upper plate to the first lower side of the lower plate;
a second lattice that connects the second upper side of the upper plate to the second lower side of the lower plate;
an opening having internal threads about a longitudinal axis between the upper plate, the lower plate, the first lattice, and the second lattice; and
a screw member comprising a shank comprising threads that engage the internal threads within the opening, the screw member having a diameter such that rotation of the screw member about the longitudinal axis moves the upper plate and the lower plate away from each other by deforming the first lattice and the second lattice and moves the first lattice and the second lattice away from each other by deforming the upper lattice and the lower lattice.

14. The expandable intervertebral implant of claim 13, wherein the upper plate, the lower plate, the first lattice, and the second lattice are made from titanium.

15. The expandable intervertebral implant of claim 13, wherein the first lattice and the second lattice each comprise a first pattern, and wherein a size of the opening, and a diameter of the screw member are selected such that rotation of the screw member about the longitudinal axis moves the screw member within the opening and expands the expandable intervertebral implant along a cephalad-caudal axis and along a medial-lateral axis to a target expanded configuration.

16. The expandable intervertebral implant of claim 13, further comprising:
 a proximal end;
 a distal end; and
 an inserter attachment feature connected to the upper plate, the lower plate, the first lattice, and the second lattice at the proximal end;
 wherein the upper lattice, the lower lattice, the first lattice, and the second lattice each comprise a portion of the inserter attachment feature.

* * * * *